US009717609B2

(12) United States Patent
Abunassar

(10) Patent No.: US 9,717,609 B2
(45) Date of Patent: Aug. 1, 2017

(54) VARIABLE STIFFNESS STENT

(71) Applicant: Abbott Cardiovascular Systems Inc., Santa Clara, CA (US)

(72) Inventor: Chad Abunassar, San Francisco, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 474 days.

(21) Appl. No.: 13/957,357

(22) Filed: Aug. 1, 2013

(65) Prior Publication Data
US 2015/0039075 A1   Feb. 5, 2015

(51) Int. Cl.
*A61F 2/06* (2013.01)
*A61F 2/915* (2013.01)

(52) U.S. Cl.
CPC .... *A61F 2/915* (2013.01); *A61F 2002/91575* (2013.01); *A61F 2250/0018* (2013.01); *A61F 2250/0029* (2013.01); *A61F 2250/0036* (2013.01); *A61F 2250/0037* (2013.01); *Y10T 29/49908* (2015.01)

(58) Field of Classification Search
CPC ............... A61F 2/82; A61F 2002/825; A61F 2002/826; A61F 2002/91541; A61F 2002/91558; A61F 2002/91566; A61F 2002/91575; A61F 2002/9522; A61F 2002/9583; A61F 2002/91525; A61F 2002/91533; A61F 2002/9155; A61F 2002/91583; A61F 2002/91591; A61F 2002/9665; A61F 2/844; A61F 2/848; A61F 2/852; A61F 2/856; A61F 2/86; A61F 2/90; A61F 2/91; A61F 2/915; A61F 2/92; A61F 2/93; A61F 2/95; A61F 2/954; A61F 2/958; A61F 2/962; A61F 2/966; A61F 2/97; A61F 2002/821; A61F 2002/823; A61F 2002/828; A61F 2002/8483; A61F 2002/8486; A61F 2002/91508; A61F 2002/91516; A61F 2002/9151; A61F 2002/9505; A61F 2002/9511; A61F 2002/9517; A61F 2002/9525; A61F 2002/9534
See application file for complete search history.

(56) References Cited

U.S. PATENT DOCUMENTS 5,514,154 A   5/1996   Lau et al.
6,066,167 A   5/2000   Lau et al.
(Continued)

OTHER PUBLICATIONS

Form. (n.d.) American Heritage Dictionary of the English Language, Fifth Edition. (2011). Retrieved Jun. 18, 2016 from http://www.thefreedictionary.com/form.*
(Continued)

*Primary Examiner* — Jonathan Miles
*Assistant Examiner* — Kankindi Rwego
(74) *Attorney, Agent, or Firm* — Squire Patton Boggs (US) LLP

(57) ABSTRACT

A stent has one or more redundant crests for a ring. The redundant crest is located at a Y-crown for a peak-to-valley type stent pattern in one example. The stent may also have frangible bridges for connecting links. The stent's radial stiffness decreases when a redundant crest fractures and its axial and bending stiffness decreases when a frangible bridge breaks.

21 Claims, 12 Drawing Sheets

(56) References Cited

U.S. PATENT DOCUMENTS

| | | | |
|---|---|---|---|
| 6,086,610 A * | 7/2000 | Duerig | A61F 2/07 623/1.18 |
| 6,206,910 B1 | 3/2001 | Berry et al. | |
| 6,258,117 B1 | 7/2001 | Camrud et al. | |
| 6,350,277 B1 * | 2/2002 | Kocur | A61F 2/90 623/1.11 |
| 6,540,777 B2 | 4/2003 | Stenzel | |
| 6,663,664 B1 * | 12/2003 | Pacetti | A61F 2/91 623/1.15 |
| 7,294,146 B2 | 11/2007 | Chew et al. | |
| 7,316,147 B2 * | 1/2008 | Perreault | A61F 2/95 29/283.5 |
| 7,357,942 B2 | 4/2008 | Burke et al. | |
| 7,625,401 B2 | 12/2009 | Clifford et al. | |
| 8,425,587 B2 | 4/2013 | Trollsas et al. | |
| 2001/0044651 A1 | 11/2001 | Steinke et al. | |
| 2002/0107563 A1 | 8/2002 | Shanley | |
| 2003/0023301 A1 | 1/2003 | Cox et al. | |
| 2003/0040771 A1 | 2/2003 | Hyodoh et al. | |
| 2003/0040772 A1 | 2/2003 | Hyodoh et al. | |
| 2003/0199969 A1 | 10/2003 | Steinke et al. | |
| 2004/0093077 A1 | 5/2004 | White et al. | |
| 2004/0254627 A1 * | 12/2004 | Thompson | A61F 2/91 623/1.11 |
| 2005/0033399 A1 | 2/2005 | Richter | |
| 2005/0125051 A1 | 6/2005 | Eidenschink et al. | |
| 2005/0149172 A1 | 7/2005 | Varma | |
| 2005/0182479 A1 | 8/2005 | Bonsignore et al. | |
| 2005/0203607 A1 | 9/2005 | Scherrible | |
| 2006/0020324 A1 | 1/2006 | Schmid et al. | |
| 2006/0122691 A1 | 6/2006 | Richter | |
| 2006/0217795 A1 | 9/2006 | Besselink et al. | |
| 2007/0027528 A1 * | 2/2007 | Agnew | A61F 2/2412 623/1.24 |
| 2007/0179599 A1 | 8/2007 | Brodbeck et al. | |
| 2007/0182041 A1 | 8/2007 | Rizk et al. | |
| 2007/0219612 A1 | 9/2007 | Andreas et al. | |
| 2007/0219642 A1 | 9/2007 | Richter | |
| 2007/0271763 A1 | 11/2007 | Huang et al. | |
| 2008/0243230 A1 * | 10/2008 | Lootz | A61F 2/91 623/1.15 |
| 2008/0275537 A1 | 11/2008 | Limon | |
| 2010/0244304 A1 | 9/2010 | Wang | |
| 2010/0256740 A1 | 10/2010 | Limon et al. | |
| 2011/0066223 A1 | 3/2011 | Hossainy et al. | |
| 2011/0230959 A1 | 9/2011 | Pienknagura | |
| 2012/0042501 A1 | 2/2012 | Wang et al. | |
| 2012/0065722 A1 * | 3/2012 | Pacetti | A61F 2/915 623/1.15 |
| 2012/0109281 A1 * | 5/2012 | Papp | A61F 2/958 623/1.15 |
| 2013/0123905 A1 | 5/2013 | Abunassar et al. | |

OTHER PUBLICATIONS

Stoeckel, D (1995) The Shape Memory Effect: Phenomenon, Alloys and Applications. In: Shape memory alloys for powers systems, EPR. Nitinol Devices and Components, Inc. 475333 Westinghouse Drive Fremont, California 94539, pp. 1-13.*

U.S. Appl. No. 13/957,357, filed Mar. 15, 2013, Hossainy et al.

* cited by examiner

VARIABLE STIFFNESS STENT

BACKGROUND OF THE INVENTION

Field of the Invention

The present invention relates to stents; more particularly, this invention relates to stents for treating vessels of the body.

Description of the State of the Art

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. Crimping refers to an iris-type or other form of crimper, such as the crimping machine disclosed and illustrated in US 2012/0042501. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

A compliance-matching stent structure exhibits a high degree of radial flexibility at the end rings of the stent. These relatively 'high compliance' end-ring structures allow the deployed stent to better match the compliance of the adjacent vessel wall, thereby providing for improved pulsatile hemodynamics. In order to also provide sufficient scaffolding support against compressed plaque, the stent structure is relatively stiff in the middle-section of the stent. An example of a compliance-matching stent is described in U.S. Pat. No. 6,206,910. While the structure described in this publication aims to utilize low end-ring radial stiffness to enable improved hemodynamics, it may not adequately scaffold plaques acutely, which is often the primary function of a deployed stent. Calcified lesions, ostial lesions, and total occlusions all require a high degree of radial stiffness to avoid localized collapse after deployment. Against these 3 challenges and others, the structure disclosed in U.S. Pat. No. 6,206,910, may not perform adequately. For example, when stenting a lesion with even a modest plaque volume, longitudinal plaque migration is known to occur. In these cases the stent should have acute radial stiffness sufficient at the ends of the deployed structure during an acute period, i.e., within the first 1-2 weeks, or month following implantation. At later timeframes after deployment, however, a stented vessel will remodel positively over time, thereby requiring less radial stiffness. For this reason, a stent structure is desired that provides high end-ring radial stiffness acutely, and low end-ring radial stiffness in the long term after vascular remodeling occurs.

There is a need for improving long term vascular healing following stent implantation without adversely affecting stent stiffness characteristics needed during an acute period following implantation. Such long-term healing has been inhibited by a stent structure no longer needed to provide vascular support or where less support is needed from the stent. However, this support is needed during the acute period. It is desirable therefore to improve upon a stent having a variable radial stiffness and/or variable longitudinal or bending stiffness so that the stiffness reduces after a predetermined amount of time has elapsed following implantation.

SUMMARY OF THE INVENTION

In response to these needs there is a stent having variable stiffness, including one or more redundant crests formed in one or more rings of the stent. The crests are formed as frangible elements, meaning they are intended to fracture. In doing so a bar arm length is increased, which reduces the radial stiffness at the crest of the ring. Prior to fracture of the crest at a crest notch, the crest of a peak portion of an undulating ring structure is made stiffer by the effective combined stiffness of the intact redundant crest and outer crest. As such, a stent may have rings with a variable stiffness. The first radial stiffness is a baseline radial stiffness with a crest stiffener provided by the addition of the redundant crest to the baseline's outer crest stiffness. The second radial stiffness, which is less than the first radial stiffness, results when the redundant crest (a designed-for frangible element) fully severs, breaks or fractures, thus becoming no longer capable of carrying loads between struts of the ring. After the redundant crest fractures the ring is less stiff as only the outer crest is capable of carrying loads between the struts.

According to one embodiment one or more redundant crests may be found at every Y-crown of a peak-to-valley stent design. The invention is not, however, limited to a peak-to-valley type of stent pattern. Moreover, a redundant crest may be formed at each ring, every other ring, or only at the ends such as in the case of an end-compliant ring.

A balloon expandable stent must have sufficient radial strength and stiffness to stent a coronary lesion and hence prevent acute vessel recoil. After this function is accomplished, a typical stent continues to exert a chronic force against the blood vessel for its implanted lifetime. It is believed that a gradual and controlled loss of stent strength/stiffness will encourage restoration of vascular motion to levels which approach native behavior of a healthy vessel. A stent according to the invention is designed to gradually reduce in stiffness within a timeframe of months after implantation. This is accomplished through redundant crests, or crest "fuses" which fracture over time, giving rise to an increase in bar-arm length or fulcrum about a crest, thereby reducing the radial stiffness of a ring. The stent can be used to accomplish Vascular Reparative/Restorative Therapy (VRT) inexpensively and without using bulk-degrading materials such as PLLA. In addition, it may be applied to bulk degrading scaffolds for added control of strength loss.

Vascular Reparative/Restorative Therapy (VRT) seeks to provide a controlled reduction in radial strength and radial stiffness throughout the implanted lifetime of a stent or scaffold. Typically, a gradual and somewhat homogeneous reduction in strength or stiffness is achieved by way of bulk material degradation in coronary applications. After a period of time has elapsed sufficient to cause a loss in molecular weight, for example, the scaffold backbone begins to breakdown causing fractures. Redundant (frangible) crests according to the invention may be utilized to achieve a similar end result. That is, a strut discontinuity formation occurring with bioresorbable material may be simulated for non-bioresorbable material, e.g., non-biodegrading metal or metal alloy backbones, to reduce stent strength at earlier or later timeframes depending on need, e.g., about six months after implantation. Thus as a VRT stent gradually loses stiffness by way of fracturing structure, the target vessel experiences reduced restriction to native vasomotion. This in turn promotes progressive improvement of vascular function and health, hence VRT. The invention is directed primarily to stents or backbones made of a non-biodegradable or non-bioresorbable structure; however, the disclosure is not limited to only non-biodegradable or non-bioresorbable structure.

Discontinuity formation for bioresorbable material such as Poly (L-Lactide) is distributed throughout the stent structure and somewhat uncontrollable. Because of this, reduction in the functional radial strength of the scaffold might be uncontrolled and may not be repeatable from patient to patient. Further, a completely discontinuous structure may produce undesired strut motion and/or scaffold piece migration. Additionally, Poly (L-Lactide) or other degrading backbones require extensive material characterization activities for static and fatigue property determination (at time=0 and at later timeframes) to safely design a robust implant. Additionally, scaffold fatigue testing cannot be accelerated-age-tested to the same levels as with traditional stents (60 Hz) since the material has viscoelastic properties. Instead, fatigue testing must be performed at much slower speeds approaching in vivo testing speeds. This slows down the development of new scaffold platforms and greatly impedes efficient learning. In addition, regulatory challenges make investing in new degrading technologies difficult, and implant cost/yield are typically high compared to conventional stents.

Forensic microscopy of fatigue-overloaded stents (fatigue-to-fracture testing) has demonstrated that fatigue fractures initiate in the stent crest features, typically on the outer edge of a stent crest (akin in load-bearing roles as an 'extrados' of a structural arch). In a preferred embodiment it has been found that a first failure mode occurs at a Y-crown (as opposed to a W-crown or U-crown). One can induce fatigue fracture by locally narrowing the width properly and/or notching a redundant stent crest at the Y-crown by a radius or V type of notch.

For a proper design of the redundant crest, with respect to local stresses and ring structure, it has been found that the fluctuating stresses experienced by the stent structure can be magnified at the redundant crest, thereby allowing for a predictable fatigue fracture at the redundant crest (as opposed to, e.g., a nearby strut). Essentially, by employing a redundant crest having a narrowed width and/or selective notch size, it has been found that one may be able to control both the location and occurrence timeframe of fatigue fractures during fatigue loading. As such, a ring can be designed to have a reduced radial stiffness triggered by the failure of one or more redundant crests but while retaining structural integrity, which means having a continuous/intact ring capable of carrying a radial load with substantially reduced radial stiffness after the redundant crest(s) fail.

In one aspect, a gradual reduction in stent radial strength and stiffness over time utilizes redundant crests that provide additional stiffness (initially) to a baseline stent pattern. The baseline pattern is made to provide low radial stiffness by the use of long, swinging bar arm features, e.g., as in the case of an end-compliant stent. With the temporary redundant crests added the radial strength is increased to a desired amount (e.g., >350 mmHg and up to an order of −1000 mmHg). Redundant crests may therefore boost radial strength acutely to required values.

In another aspect, the size of a notch and/or shape of a redundant crest may vary from ring-to-ring, or a ring may be devoid of a redundant crest but its neighbor has redundant crests. These designs can encourage early and late failure, or failure of redundant crests for only a portion of the stent, e.g., at the ends.

According to another aspect, a stent having one or more redundant crests may further include a variable longitudinal stiffness. After deployment, an implanted stent must have sufficient axial stiffness to resist longitudinal stent deformation (LSD) induced by guide contact or crossing with another device. In addition, deployed stents must be highly flexible to conform to arterial curvature while also resisting fatigue under arterial bending loads. Unfortunately, these two attributes, stent axial stiffness (LSD resistance) and bending flexibility are typically inversely related. This creates a critical design trade-off for stent designers. To meet this need, a stent link structure includes one or more redundant, frangible bridges that when fractured reduce the axial and bending stiffness. In this way, a stent is produced with high acute LSD resistance when crossing events are likely; and increased bending flexibility and conformability in the long term timeframe (6 months+). Longitudinal stent deformation (LSD) resistance describes a deployed stent's ability to resist crumpling when pushed or pulled in the axial direction when crossing with another device, guide contact, or device withdrawal. See e.g., US 2013/0123905. The issue of LSD is prevalent for highly flexible 2-link stent platforms. Stent flexibility is another sought-after stent design characteristic, and is typically superior for stent platforms with fewer links, narrower links, and thinner struts. Not surprisingly, these design features which provide flexibility do so at the detriment of LSD resistance. Therefore, a difficult design tradeoff exists between LSD resistance and bending flexibility/conformability.

In one aspect there is a redundant bridge structure for a link. The bridge(s) add additional longitudinal/bending stiffness to a link possessing a long U-shape feature. The bridge reduces the moment arm of the U-shape (the moment arm being about the length from the neutral axis of the link's straight portion to the neutral axis of the crest of the U-portion), effectively making a shorter U, thereby increasing the axial/bending stiffness while the bridge remains intact. The period following implantation may be adjusted by increasing or reducing a notch size, or increasing/decreasing the width of the bridge. Or there may be a plurality of bridges spanning the U when a relatively high axial stiffness is needed during an acute period.

According to another aspect a redundant crest or variable stiffness ring is made at the end rings or only the end rings, such as in the case of a compliance-matching stent or a stent having longer ring widths than the ring widths interior to the end rings. Prior to fracture at the notch, the end rings may have a radial stiffness relatively equal to, about less than, about the same, or about greater than the radial stiffness of rings located inboard or in the middle of the stent structure. After the notch breaks, the radial stiffness of an end ring is substantially smaller than the radial stiffness of an inboard ring, or a ring adjacent to the end-ring. The redundant crests fracture so that the stent may provide greater compliance, or more compatibility with adjacent unsupported native vessel properties.

According to another aspect a variable stiffness ring has a variable longitudinal or bending stiffness for links connecting an end ring. The need to increased longitudinal stiffness at the end rings (ie. strategic placement of redundant links at the ends of the stent) would help prevent LSD specifically, as crossing devices often catch at the proximal end. Also, the proximal end of a device is likely to be the portion that is mal-apposed (if any), due to luminal tapering. To address this problem, prior devices have stiffened end rings (e.g., adding more links, such as 4 links as compared to 2 links at the interior). The support is needed at the ends, especially for highly flexible 2-link stent patterns. However, this stiffening method provides the increased longitudinal stiffness indefinitely. There is no mechanism for reducing the stiffness when the support is no longer wanted.

According to one aspect of the invention, there is a stent or scaffold, medical device, method for making such a stent or scaffold, or method for assembly of a medical device comprising such a stent or scaffold having one or more, or any combination of the following items (1)-(32):

(1) A redundant bridge or redundant crest includes either a v-notch or a radius notch. The V-notch has a radius of about zero. The minimum width of a redundant crest for either notch type is, or is about 10%, 25%, 50%, and 62.5% of the minimum width or width of the member that was formed into the redundant crest; the width of the crest may be about 80% of the width of a nearby strut or the outer crest; and/or the minimum width of the redundant crest is at most 60%, or between about, or between 50-60% of the width of the outer crest or nearby strut (2) A redundant crest is found on a Y-crown, or only a Y-crown, or either or both of a Y-crown and a W-crown for an end ring, or a U crown.

(3) A crest has an eyelet, hole, closed space or opening circumscribed by surfaces of a redundant crest, outer crest and strut portions. The surface circumscribing hole may be circular-like (FIG. 3A), semi-circular with V-shape extending into the space (FIG. 3B), or a teardrop shape. The closed shapes described refer to the closed space prior to forming the notch.

(4) For a ring of a stent where local maximum bending stresses occur at the crown, the stresses are due primarily to a moment F×BA1 after the redundant crest fractures and F×BA2 before the crest fractures (BA1>BA2). "BA1" and "BA2" are bar arm lengths, moment arms or fulcrums measured between a crest and a trough. The stiffness at the crest decreases by a factor equal to about BA1/BA2 when the redundant crest fractures. In preferred embodiments the factor BA1/BA2 is, or is about 5/6, 4/5, 2/3, or 3/4. For a compliant ring stent the factor BA2'/BA1' at an end ring is, or is about 1/6, 2/5, 1/3, or 1/4 and for an adjacent or inner ring there is no redundant crest or the factor BA1/BA1 is, or is about 5/6, 4/5, 2/3, or 1/4.

(5) A redundant crest satisfies five criteria: (i) maximum stress always occurs at the redundant crest notch, rather than nearby areas such as the strut connecting the crest to a trough; (ii) failure occurs at the notch before failure anywhere else on the peak or crown; (iii) after substantially total failure of the crest (i.e., the crest is no longer capable of carrying loads between the struts) maximum stress transfers to the outer crest. Thus, the outer crest remains intact after fracture and continues to carry load between struts; (iv) the LFSF decreases, or there is a proportional increase in fracture rate (or reduced cycles needed for fracture) with increasing notch size so that a notch size is increased or decreased over a nominal size (or no notch is used for the redundant crest) depending on when fracture is desired after implantation or after n radial cycles, such as two weeks after implantation, two months, six months etc.; and (v) when the notch fractures the outer crest stiffness decreases by the factor (BA1/BA2); and (vi) a crimped diameter, or crossing profile diameter is not inhibited with the presence of the redundant crest. A diameter reduction of about 2.0 or greater is preferred.

(6) A redundant crest as substantially shown in any of FIGS. 3A, 3B and 3C for suitable notch sizes satisfying criteria (i) through (vi) for the designs.

(7) A redundant crest located at a peak of a Y-crown, all Y-crowns of a stent, or all Y-crowns of a ring.

(8) A redundant crest is a frangible element by having a minimum width of 80% or about 80% of the outer crest or strut width without a notch being formed; or with a V or radius-type notch.

(9) A flat or straight redundant crest, and/or a redundant crest that is angled towards the outer crest or angled inward, or into the space surrounded by the outer crest, redundant crest and upper and lower strut portions.

(10) Fatigue acceleration, drop in LFSF, or rate of change of LFSF for each of the notch sizes as shown in TABLE 1.

(11) A redundant crest having about, or having a 0%, 25%, 50% or 62.5% notch size. A stent can have some redundant crests with a 50% or about 50% notch size and other crests with less or more than this notch size, such as when the stent is an end-compliant stent (higher notch size at end rings).

(12) Before a notch is formed, a redundant crest having a width at the notch center/location is, or is about 80% of the width of a strut, crest or a trough.

(13) For a redundant crest with a notch, the notch faces the outer crest so that fatigue fracture occurs as a result of radial compressive cycles of the expanded stent supporting the vessel.
(14) LINKS: A stent link structure including one or more redundant, frangible bridges that when fractured reduce the axial and bending stiffness. For example, a U-shaped link having one, two or three bridges that bridge the ends of the U shape of the link. When a bridge fractures the axial and bending stiffness provided by the link decreases.
(15) The U link with one or more bridges forms a W-crown and Y-crown when connecting rings.
(16) A change in bending stiffness of a U-link when one or more bridges fracture may be, or is about (D2/D1), which can be equal to ½, ⅓, ¼, ⅕ or ⅙. Where the D1 is the distance between the crest of the U and straight portion and D2 is the distance between the bridge and straight portion; and/or the width of a U portion of a link with one or more bridges may be about, or is 80% of the width of the connecting or straight portion of a link or the width of a ring's crest.
(17) One or more frangible bridges includes a V-notch or radius notch facing towards or away from a crest of a U-portion of a link. The sizes of the notches can be constant, or may vary when more than one bridge spans a U portion of a link.
(18) A U-link with one or more frangible bridges as substantially shown in FIGS. 4A, 4B, 5A and 5B.
(19) Plural bridges (e.g., 2, 3) bridging the U portion of a link. The notch sizes may or may not vary. A deeper notch for bridges having a lesser moment arm with respect to the straight portion so that the substantially higher axial stiffness provided by the bridge fractures quickly, whereas the other bridges fracture after a longer period, e.g., no sooner than 1 month. For example, the minimum width at a notch can be about, or can be ½ or ⅓ the minimum width at other notches.
(20) PATTERN: A stent pattern having one or more types of redundant crests, where the stent pattern is a "peak-to-valley" link connection.
(21) A stent having some rings with redundant crests and some without, such as described in FIG. 6. There can be 1, 2, 3, or 4 rings without a redundant crest between each ring with a redundant crest.
(22) A stent having links with one or more frangible bridges. There may be frangible bridges for one or all links extending between two adjacent rings depending on the amount of reduction in axial stiffness desired. Or depending on the number of links.
(23) An end compliant ring having first and second end-rings, wherein the end-rings' width are substantially greater than the width of the adjacent ring or any interior rings of the stent.
(24) Links having one or more frangible bridges elements for only those links connecting an interior ring to an end ring. The stent may have 2, 3, 4 or more links between each ring.
(25) The ratio of bar arm lengths BA2'/BA1' for an end-ring is substantially smaller than the ratio of bar arm lengths BA2/BA1 for an interior ring; BA2' is about equal to BA2 so that BA1'>BA1; and/or there is a redundant crest only at the end rings.
(26) A method of crimping, or a crimped stent. The stent having rings with redundant, frangible crests. The stent is plastically deformed from the as-cut diameter (formed form a tube) to a fully crimped diameter and the crimping reduces the diameter by a factor of about 2.0. The stent is crimped to a balloon of a balloon catheter.
(27) A stent having a circumference and an axis, including a pattern of interconnected elements forming a plurality of rings, wherein rings comprise struts, rings are connected to adjacent rings by links and each ring extends about the circumference in an undulating pattern of alternating peaks and valleys; and at least one of the peaks and valleys comprising: an outer crest of a peak and an outer trough of a valley, wherein a distance between the outer crest and the outer trough is a width of the ring, a first strut extending from the outer crest to the outer trough of a first adjacent valley and a second strut extending from the outer crest to the outer trough of a second adjacent valley, the peak including a redundant crest, the redundant crest extending between the first and second struts, a notch formed on the redundant crest, a first radial stiffness when the notch is severed, and a second radial stiffness, higher than the first radial stiffness, when the notch has not severed, wherein the peak is configured such that the outer crest is capable of carrying radial loads between the first and second struts substantially intact after the redundant crest substantially fails.
(28) In combination with items (27), (29), (30) or (31), any of the following things individually or in any combination: wherein the stent includes end-rings and an interior ring located between the end rings, wherein the interior ring is devoid of a redundant crest and has a first bar arm length, and after a notch of at least one of the end rings sever, a bar arm length of the end ring increases from a second bar arm length to a third bar arm length, wherein the third bar arm length is substantially greater than the first and second bar arm lengths; wherein the stent includes end-rings and an interior ring located between the end rings, wherein the width of an end ring is greater than the width of the interior ring, and wherein the end ring peak has first and second bar arm lengths before and after, respectively, an end ring notch severs, and the interior ring peak includes third and fourth bar arm lengths before and after, respectively, an interior ring notch severs, wherein the first and fourth bar arm lengths are about equal and the second bar arm length is greater than the fourth bar arm length; wherein a notch of the end ring is greater than a notch of the interior ring; wherein the notch has an inner radius of about zero; wherein the redundant crest, outer crest and struts form a closed space; wherein the redundant crest forms a substantially straight surface or continuous curve portion along an edge of the closed space; wherein the redundant crest is angled inwards towards the outer crest; wherein a link connects a peak to a valley; wherein the links are U-shaped links comprising a U-portion disposed between a first and second ring, further including one or more frangible bridges spanning between arms of the U-portion; wherein the one or more bridges having a width of about 80% of the width of a straight portion or the U-portion of the U-shaped link; wherein the one or more bridges include a notch facing towards and/or away from the U-portion; wherein the notch reduces the thickness of the redundant crest by about, or by 25%, 50% or 62.5%; the redundant crest comprising a structure configured for fracturing at the notch prior to fracture at a strut portion adjacent the redundant crest, the structure including: a crest width that is, or is about 80% of the width of the first strut, the outer crest or outer trough, and a notch width that is, or is about 25%, 50% or 62.5% of the crest width; the redundant crest comprising a structure configured for fracturing at the notch prior to fracture at a strut portion adjacent the redundant crest, the structure including a notch width is at most about, or is at most 60% of a width of the first strut, the outer crest or outer trough; the redundant crest comprising a structure configured for fracturing at the notch prior to fracture at a strut portion adjacent the redundant crest, wherein the peak includes a closed space formed by a portion of the first and second struts, the redundant crest and the outer crest, wherein the redundant crest is straight, angled away from the outer crest or angled towards the outer crest; wherein the redundant crest is angled towards the outer crest, the notch size is, or is about 25%, 50% or 62.5% of the redundant crest width and the lowest fatigue safety factor (LFSF) decreases monotonically with increasing notch size; and/or wherein the redundant crest width is, or is about 80% of an outer crest width or a first strut width.

(29) A method for crimping the stent as described in (27), (28), (30) or (31) to a balloon of a balloon catheter, including the steps of reducing the diameter of the stent by plastic deformation of the stent, wherein the stent has a pre-crimp diameter before crimping and a fully crimped diameter after crimping, and wherein the ratio of pre-crimp to fully crimped diameters is at least about 2. The redundant crest may be angled towards the outer crest.

(30) A stent, including a pattern of interconnected elements forming a plurality of rings, wherein rings comprise struts, rings are connected to adjacent rings by links and each ring extends about the circumference in an undulating pattern of alternating peaks and valleys; at least one of the rings comprises a variable stiffness ring, including: an outer crest and an outer trough of a valley, wherein a distance between the outer crest and the outer trough is a width of the ring, a first strut extending from the outer crest to the outer trough of a first adjacent valley and a second strut extending from the outer crest to the outer trough of a second adjacent valley, the peak including a redundant crest, the redundant crest extending between the first and second struts, and a notch formed on the redundant crest, wherein a radial stiffness of the peak is proportional to a bar arm length between a load-bearing valley crest and a load-bearing peak crest, so that the variable stiffness ring has a first stiffness when the redundant crest is severed at the notch, and a second stiffness when the redundant crest has not severed at the notch, the second stiffness being higher than the first stiffness, and wherein the peak is configured such that the outer crest is capable of carrying radial loads between the first and second struts substantially intact after the redundant crest substantially fails.

(31) In combination with items (27), (28), (29), or (30), any of the following things individually or in any combination: wherein the rings comprise a pair of end rings and rings adjacent and interior to the end rings, the end rings comprising a variable stiffness ring at only the end rings; wherein the stent includes a pair of end rings and rings adjacent and interior to the end rings, the end rings comprising a first variable stiffness and the inner rings comprising a second variable stiffness, different from the first variable stiffness, such that the radial stiffness of the end rings is substantially lower than the radial stiffness of the inner rings after the redundant crests substantially fail for the end and inner rings; wherein the end rings have a first variable stiffness and the interior rings have a second and a third variable stiffness, different from each other and each being substantially greater than the first variable stiffness after the respective redundant crests substantially fail; and/or wherein the rings having the third variable stiffness are closest to the end rings and after the redundant crests substantially fail the stiffness of the third variable stiffness rings is substantially less than the stiffness of the second variable stiffness rings.

(32) In combination with items (27), (28), (29), or (30), a stent configured for providing a side cell opening, wherein rings with redundant crests are at least located internally of end rings and surrounding at least a partial hole in the stent to provide a structure that expands during side-cell opening. In one example the stent has removed the struts forming ring 12*b* extending above the middle links in FIG. 1 and removing the links 34 as well, so that there are only 4 links (as opposed to the normal 6) between 12*a* and 12*c*, an open space is above the middle links and the ring 12*b* extends only between the bottom-most and middle links. In this embodiment only the rings 12*a*, the remaining part of 12*b* and 12*c*, or only the 2 or 3 rings nearest the hole or opening between rings 12*a*, the remaining part of 12*b* and 12*c* have redundant crests and/or frangible bridges; or the ratio BA2/BA1 is greater for 12*a*, the remaining part of 12*b*, 12*c* or the nearest 2 or 3 rings as those rings are wider than rings further from the opening or hole. The redundant crests and/or links with frangible bridges after substantial failure would cause the opening to open more readily, thereby effectively widening the hole for side-cell openings (for side branch access), permitting a larger circular profile structure to pass through. Rings and links remain substantially intact, yet become substantially more flexible so as to provide easier branch access and without disturbing flow dynamics near the branch.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Figure 1:
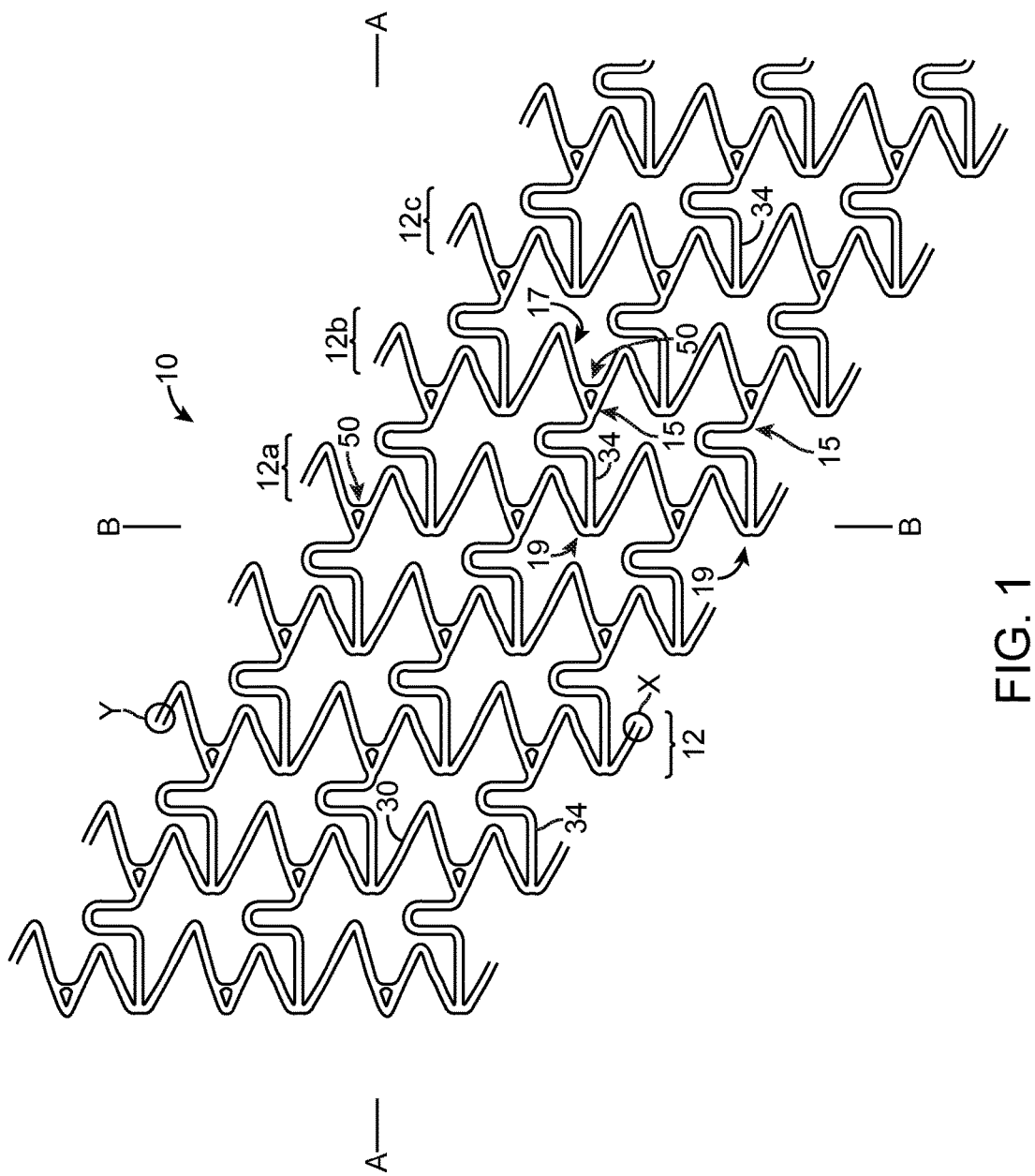
FIG. 1 shows one example of a balloon-expanded stent according to the disclosure. The stent is illustrated as a pattern in this figure, as well as for the stents depicted FIGS. 6-10. In this example, each ring has 6 crowns and rings are connected to adjacent rings by 3 links. Each link is separated by 120 degrees. The drawing is a planar view showing the repeating pattern. An end of the stent is shown on the left. The rings 12 circumscribe a bore or the stent. To help with visualizing the tubular structure described by this pattern, note the strut portion "x" is the same strut as strut portion "y".

For purposes of this disclosure, the following terms and definitions apply:

The term "about" means 20%, 10%, 5%, 4%, 3%, 2%, 1.5%, 1%, between 1-2%, 1-3%, 1-5%, 0.5%-5%, or 0% (as will be understood about 0% implies, e.g., within machine tolerance, round-off error or measurement capabilities, but devoid of absolute mathematical precision) less or more than, less than, or more than a stated value, a range or each endpoint of a stated range, or a one-sigma, two-sigma, three-sigma variation from a stated mean or expected value (Gaussian distribution).

"Axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. Thus, a link spaced 180 degrees from another link means 180 degrees as measured about the circumference of the tubular construct.

"LFSF" refers to a lowest fatigue safety factor as determined by the Goodman Criteria. See http://www.tech.plymouth.ac.uk/sme/desnotes/fatiguecalc.htm "Radial" refers to a direction, orientation, or line that is perpendicular or substantially perpendicular to the central axis of the stent or the central axis of a tubular construct and is sometimes used to describe a circumferential property, i.e. radial strength.

A "neutral axis" is the line in a beam or other member subjected to a bending action in which the fibers are neither stretched nor compressed or where the longitudinal stress is zero. A neutral axis for a beam having a constant-cross section over its length may be found from the moments of inertia of a cross-section. For example, for a square cross-section of width equal to 1 inch, the neutral axis is located at 0.5 inch or equidistant from the ends.

A "stent" is a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

"Radial strength" and "radial stiffness" adopts the definitions found in Ser. No. 13/842,547 filed Mar. 15, 2013.

The term "notch" as used throughout means a frangible or weakened portion of a stent ring or link that is intended to break, fracture or sever and thereby cause an immediate change in the local stiffness, i.e., the radial stiffness. A notch is found on a redundant crest, in the case of a ring, and a bridge in the case of a link. A notch has a minimum width spanning the element that is significantly smaller than a nominal width of the element (e.g., a crest or strut element). As will be understood by one of ordinary skill in the art, a nominal width is at least as wide as predicted to satisfy avoidance-of-failure or survivability width for the element, which is the predicted strength needed to avoid failure multiplied by a safety factor, such as 3. As compared to the nominal or minimum required width to prevent fracture in an adjacent strut, crest or link (including a safety factor), a notch width can be equal to, or can be about 25%, 50%, 10%, 75%, 62.5%, 50-60% or 25-70% of this nominal width.

The stent example of FIG. 1 may be formed from a metal or metal alloy tube laser cut to make the pattern as shown. It is understood that a stent according to the disclosure is not limited by the number of crowns per ring or links connecting rings shown in FIG. 1 or FIGS. 6-10, nor by the illustrated "peak-to-valley" configuration.

The pattern 10 of FIG. 1 represents in planar view a tubular stent structure with an axis A-A parallel to an axial direction or longitudinal axis of the stent. A radial or circumferential direction/axis B-B (perpendicular to axis A-A) for the stent is shown. The stent comprises an open framework of struts and links that define a generally tubular body. The pattern 10 includes longitudinally-spaced rings 12 formed by struts 30. A ring 12 is connected to an adjacent ring by several links 34, each of which extends parallel to axis A-A. In this embodiment of a stent pattern (pattern 10) four links 34 connect the interior ring 12, which refers to a ring having a ring to its left and right in FIG. 1, to each of the two adjacent rings. Thus, ring 12b is connected by three links 34 to ring 12c and three links 34 to ring 12a. An end ring is shown at the far left in FIG. 1. This end ring is connected to only the ring to its right in FIG. 1.

Figure 4A:
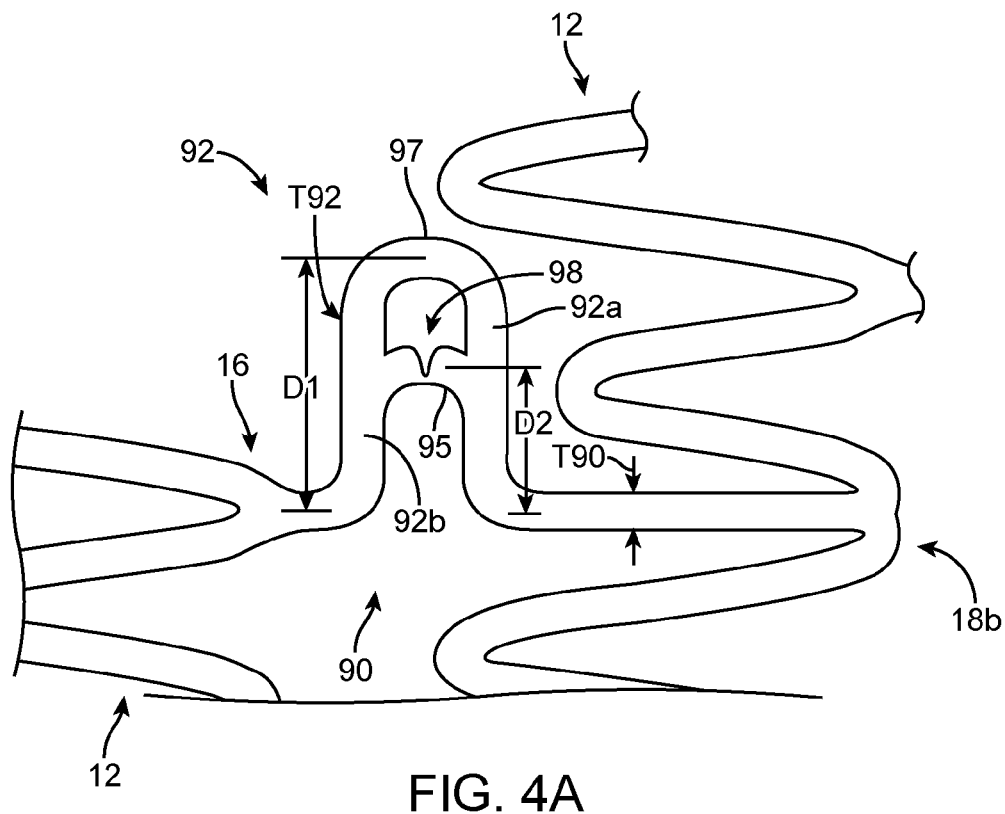
FIGS. 4A and 5A shows a link for a stent having one frangible bridge spanning a U portion. A notch faces towards or away from the crest of the U portion.

A ring 12 is formed by struts 30 connected at crowns 17, 19 or 15. A link 34 connects adjacent rings, e.g., ring 12a to ring 12b. The link 34 is joined with struts 30 at a crown 19 (W-crown) on one end and a crown 15 (Y-crown) at the opposite end. A link 34 may be straight or include a U-shaped portion with or without a frangible bridge, e.g., such as shown in link 90 (FIG. 4A). A crown 17 (free-crown or U-crown) does not have a link 34 connected to it. For each ring 12, the struts 30 that extend about the ring are joined to each other at crowns 15, 17 or 19. The struts and crowns form a circular ring of struts that extend about the circumference of the stent in an undulating pattern of alternating peaks and valleys.

Figure 2A:
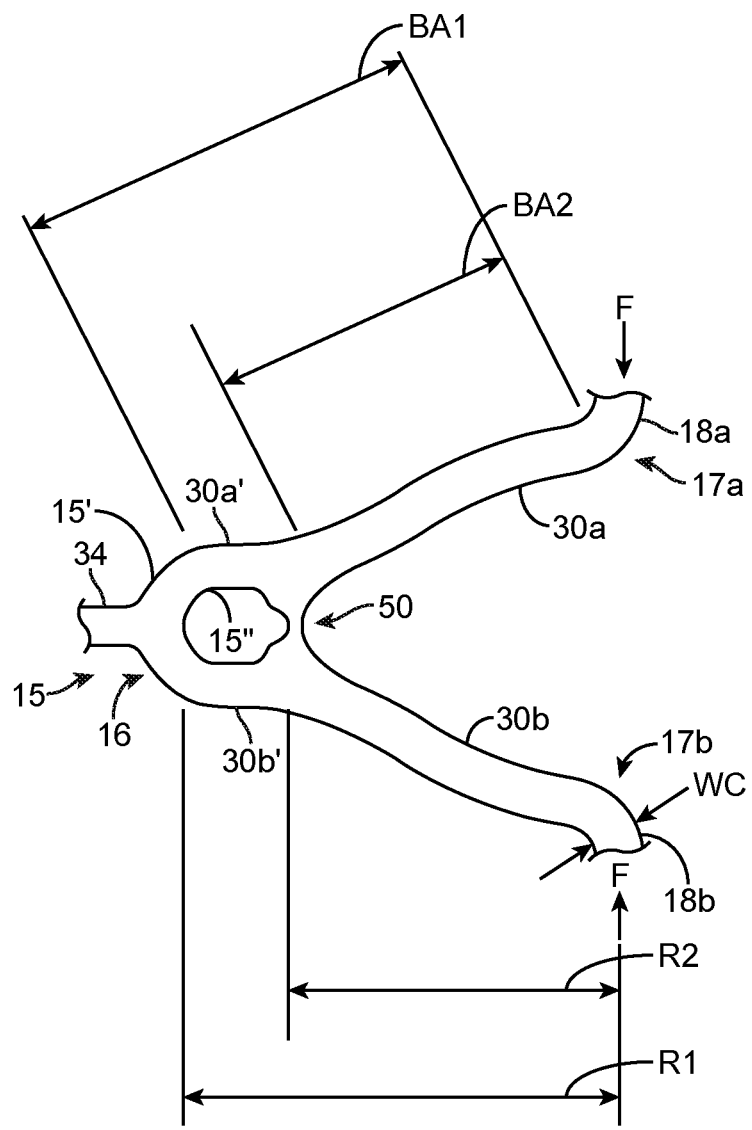
FIGS. 2A-2B show a Y-crown portion of a ring showing a redundant crest placed near an outer crest of the Y-crown.
Figure 2B:
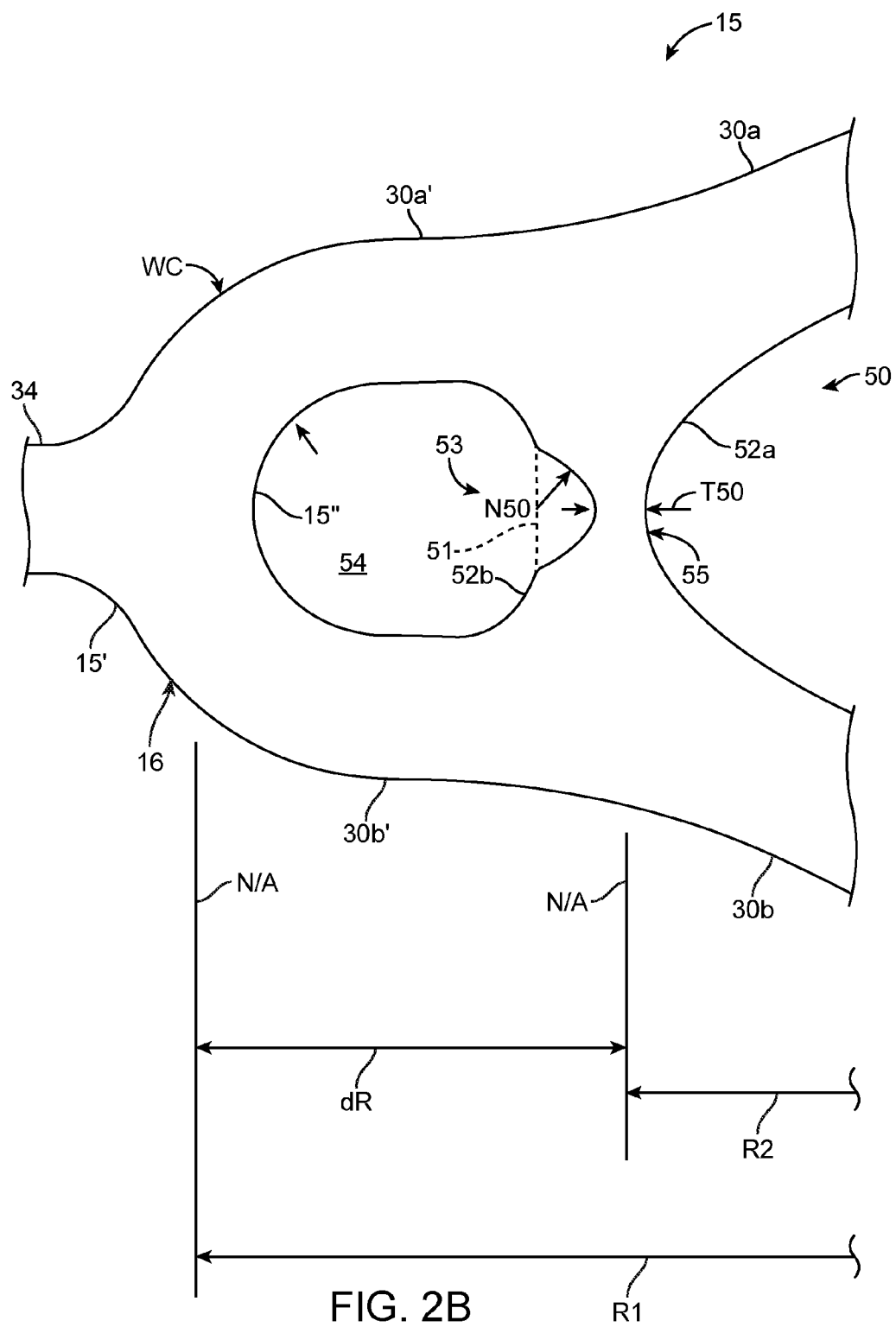

Referring to FIGS. 2A-2B there is close-up view of a Y-crown 15 and one-half of an adjacent upper U-crown 17a and lower U-crown 17b. The Y-crown 15 is a peak and the adjacent U-crowns 17a, 17b valleys. A peak forms a crest (e.g., crest 16 in FIG. 2A) and a valley forms a trough (e.g. troughs 18a, 18b in FIG. 2A) for a ring 12. A trough of a valley adjacent a Y-crown 15 is a U-crown 17 for a peak-to-valley pattern in a preferred embodiment. A crest of a peak can be a crown 15, 17 or 19 depending on the link connectivity. For the FIG. 1 pattern a crest connected to a link 34 is either a W crown 19 or Y crown 15.

The crest of the crown 15 is joined to the trough of the upper crown 17a and the trough of the lower crown 17b by struts 30a and 30b, respectfully. A width WC may be about the same for the outer crest 16 and troughs 18a, 18b. A ring 12 has a first length R1 and a second length R2 as measured along the axis A-A in FIG. 1. The first length R1 is measured between about the neutral axis (N/A) of the crest of crown 15 (alternatively, the outer surface 15' or the inner surface 15" of the crest of crown 15) and the N/A of the upper or lower trough of the valley 17a/17b (alternatively, the outer surface 17' or inner surface 17" of the trough). The second length R2 is measured from the N/A of the upper or lower trough of the valley 17a/17b (alternatively, the outer surface 17' or inner surface 17" of the trough) and the N/A of the narrowest portion of the redundant crest 50 (where the width T50 is measured) or, alternatively, about the inner surface 52a or outer surface 52b of the redundant crest 50. The difference in length between R1 and R2 is dR.

The crest of a Y-crown 15, as shown in detail in FIGS. 2A-2B, provides a variable radial stiffness at a crest for a ring 12. The variable stiffness is provided by way of a redundant crest 50 that is configured to fracture, or sever after the stent is implanted within a mammalian vessel and undergone several cycles of radial compressive loading within the vessel. Variable radial stiffness in accordance with the disclosure is preferably formed at a Y-crown. Fatigue testing has shown that stents having a pattern of U, W and Y crowns have an expected first fatigue failure at the Y-crown. It is because the first expected fatigue failure occurs at the Y-crown that makes the Y-crown a preferred location for a redundant crest. Additionally, it is preferred to have the notch 53 located on the outer surface of crest 50 (or facing crest 16) based on observed first fracture modes for a ring. The first fracture mode is radial compression for a balloon-expanded stent. Thus, to promote fracture first at the redundant crest the notch is placed on the crest 50 side subjected to fluctuating tensile stresses during cyclic radial compression of the ring 12.

The crest of the Y-crown 15 includes an outer crest 16 and the redundant crest 50 having a minimum width T50 and notch 53, which may be described by a V or radius notch 53 having the notch depth N50 and minimum width T50 (where stress concentrations causing fracture are planned to occur). The notch 53 forms a frangible element of minimum width T50 that is intended to fracture prematurely, or before any other part of the peak formed by the Y-crown 15 fractures after several cycles of a radial-compressive force applied by a vessel on the stent. FIG. 2B shows a notch defined by a radius with center at the crest 50 surface 51 (in phantom), which is the outer surface before the notch 53 was made. Thus, N50 indicates the depth of notch made in the member that became the redundant crest 50. The crest 15 has an eyelet, hole, or opening 54 circumscribed by surfaces of the redundant crest 50, outer crest 16 and strut portions 30a, 30b. The surface circumscribing hole 54 may have opposed straight or curved surfaces, such as a continuous curved surface, portions formed by strut portions 30a', 30b' and opposed inner and outer surfaces of crests 16, 50, respectively, that each substantially, or each trace the arc of a circle (with respect to crest 50, the arc of the circle is described by the surface 51, i.e., before the notch 53 was made).

A first length BA1 of the strut 30a is measured from the start of the trough crest 18a or 18b to the start of the peak outer crest 16. A second length BA2 of the strut 30a is measured from the start of the trough crest 18a or 18b to the start of the redundant crest 50 is BA2. The difference in bar arm lengths BA1, BA2 corresponds to strut portions 30a' or 30b'.

The structural properties and equilibrating forces of the Y-crown 15 having a variable radial stiffness is now explained in more detail by reference to the free-body in FIG. 2A. In essence, local maximum bending stresses at the crown 15 are due primarily to the moment F×BA1 after the redundant crest 50 fractures (at the place of minimum width T50) and F×BA2 before the crest 50 fractures. Similarly, after the redundant crest 50 fractures, there is a decrease in local bending stiffness. The change in bending stiffness at the crest may be approximated by the factor (BA2/BA1). The term "local bending moment" or "local bending stiffness" refers to the bending moment and stiffness at the Y-crown based on the free-body shown in FIG. 2A. Thus, with reference to the free-body diagram the bending stiffness of the crown 15 effectively decreases when the redundant crest 50 fractures, because the moment arm increases from BA2 to BA1. While the exact distribution of the stresses or change in stiffness will not precisely adhere to these relationships, for most purposes the ratio of BA2 to BA1 can be a good enough approximation to judge the change in stiffness for a ring 12 to enable one of ordinary skill to design a variable stiffness ring (based on a redundant crest) as needed by varying BA1 and BA2. In some embodiments if a small change in radial stiffness is desired after the crest 50 fractures, the lengths BA1 and BA2 are not substantially different (crest 50 is closer to crest 16). If a large change in radial stiffness is desired, BA1 is substantially longer than BA2. For example, BA2 is, or is about ⅚, ⅘, ⅔, ¾ of the length BA1 (i.e., portion 30a' or 30b is ⅙, ⅕, ⅓ or ¼ of the total length from outer crest to trough) according to embodiments. The rings 12 are capable of being collapsed to a smaller diameter during crimping and expanded to a larger diameter during deployment in a vessel. In one embodiment the stent was reduced from a diameter of 0.075" as formed to 0.039" as crimped. The diameter reduction for the stent may be, or is 2.0 between as-formed and fully crimped to a balloon using, e.g., an iris-type crimper which plastically deforms the stent structure form the as formed (or as cut) diameter of the stent to the fully crimped diameter.

It is desirable to have a crest 50 that enables selective design for fatigue-induced fracture as a function of the notch size; that is, allows one to form a Y-crown 15 having a variable radial stiffness that predictably fractures at a frangible crest sooner or later based primarily on the depth of the notch 53 chosen. This may allow one to essentially tune or have a built-in "fuse" for fatigue fracture of a redundant or frangible crest depending on the clinical need. Moreover, the goal is to fracture at a crest as opposed to elsewhere, so that the ring retains the ability to carry a load through its struts. In this way, one can scale the change in stiffness based on the moment arm lengths BA1, BA2 (discussed above) or desired stiffness at the crown. Essentially, the ring stiffness is changed by increasing the bar arm, moment arm, strut length or fulcrum about the hinge (crest), thereby reducing the radial stiffness. A redundant crest study seeks to find a structure that meets all of the following criteria:

i. Maximum stress occurs at the redundant crest 50 notch 53, rather than nearby areas such as the strut connecting the crest to a trough.
ii. Failure occurs at the notch 53 before failure anywhere else on the crown 15.
iii. After failure of the crest 50 maximum stress transfers to the outer crest. Thus, the outer crest 16 remains intact after fracture; thus, the crest 16 continues to carry loads to/from the link or between the struts 30$a$, 30$b$ after total failure of the redundant crest.
iv. The LFSF decreases monotonically with increasing notch size so that a notch size can be selected depending on when fracture is desired, such as two weeks after implantation, two months, etc.
v. The bending stiffness at the crest decreases by a factor of about (BA2/BA1); thus the crest effective bending stiffness prior to crest failure may be thought of as the combined stiffness of the structure including crests 16, 50 and strut portions 30$a'$, 30$b'$ and after failure only crest 16.
vi. A crimped diameter or crossing profile diameter can still be attained, or not substantially inhibited with the presence of the redundant crest. A diameter reduction of at least about 2.0 or 2.0, or greater is preferred.

Three possible designs—Design A, B and C—for the redundant crest 50 were fabricated and tested to determine which could best satisfy these criteria.

Figure 3A:
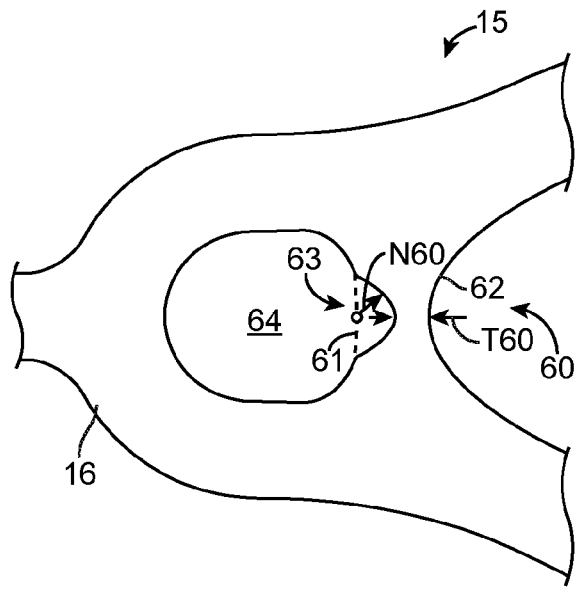
FIG. 3A shows a portion of a peak of a ring with a Design A-type redundant crest. The notch size shown is a 50% notch.
Figure 3B:
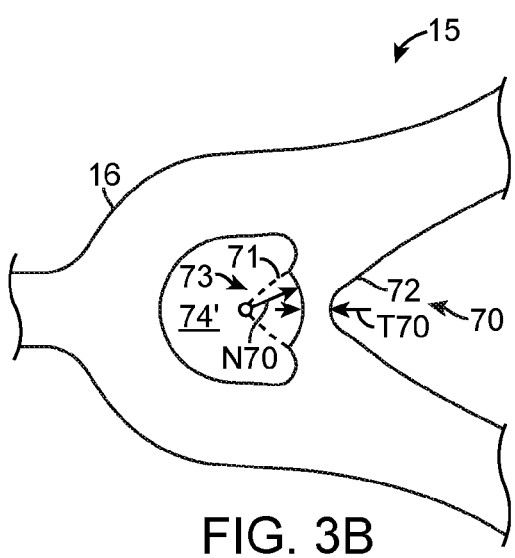
FIG. 3B shows a portion of a peak of a ring with a Design B-type redundant crest. The notch size shown is a 50% notch.
Figure 3C:
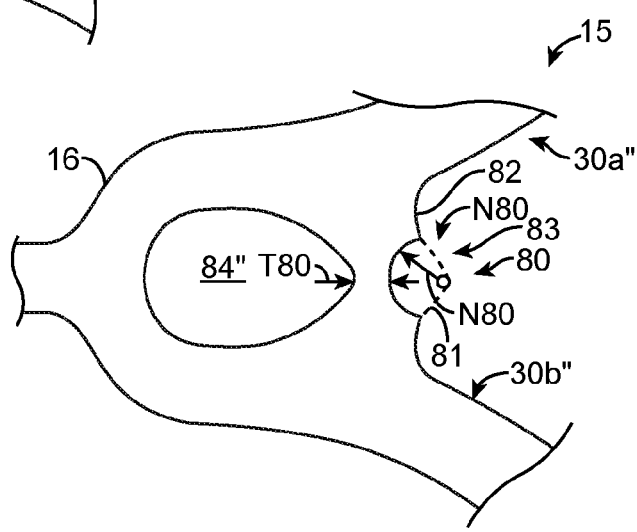
FIG. 3C shows a portion of a peak of a ring with a Design C-type redundant crest. The notch size shown is a 50% notch.

FIGS. 3A, 3B and 3C show the three designs considered. Design A, shown in FIG. 3A has a redundant crest 60. Prior to forming the notch 63, the crest 60 may be described as having a substantially straight, curved or straight interior wall surface 61 and rounded or circular-shaped exterior wall surface 62. Prior to forming the notch 63, the interior surface 61 gives the eyelet or hole 64 an approximately round or circular shape (as in the case of FIG. 2A-2B). The notch 63 is formed on the inner wall 61. The notch 63 is defined by a radius N60 with center at the location of wall surface 61. The place of minimum width is T60.

Design B, shown in FIG. 3B has a redundant crest 70. Prior to forming the notch 73, the crest 70 may be described as forming a crested inner surface 71 extending into the space 74 and V-shaped exterior wall surface 72. Prior to forming the notch 73, the interior surface 71 extends towards the inner surface of the crest 16. The notch 73 is formed on the inner wall 71. The notch 73 is defined by a radius N70 with center at the location of wall surface 71. The place of minimum width is T70. When forming the notch the portion of the wall portion protruding towards the crest 16 is partially or fully removed, as shown in the drawing.

Design C, shown in FIG. 3C has a redundant crest 80 that extends away from crest 16, as opposed to towards the crest 16, as in the case of crest 70. Prior to forming the notch 83, the crest 80 interior wall surface 81 forms a V-shaped surface and peaked or crested exterior surface 82 that extends away from the crest 16. For Design C the space 84 is tear drop shape. The notch 83 is formed on the outer wall 81. The notch 83 is defined by a radius N80 with center at the location of wall surface 81.

The place of minimum width is T80. Both crest 70 and 80 may be thought of as angled redundant crests. Crest 60 may be thought of as a flat or curved crest, or crest forming a continuous curved with the nearby connecting strut 30$a$, 30$b$, as can be appreciated from surfaces 61 and 62. Crest 80 is angled away from crest 16. Crest 70 is angled towards crest 16 or angled inward, or into the space 64. These angled crests can be appreciated from surfaces 71, 72, 81 and 82 respectively.

The inner surface contours of the crest—i.e., flat or rounded (Design A), angled towards the crest 16 (Design B) or angled away from the crest 16 (Design C) are apparent even with a sizable notch made, as would be understood through inspection of the shapes of the surfaces on the opposing side of the crest, i.e., surfaces 62, 72 and 82, remaining portions of the crest near where the notch is made, and the minimum width of the crest prior to forming the notch (e.g., about 80% of crest 16 width).

Designs A, B, and C were evaluated for their ability to satisfy the criteria (i)-(vi). To this end, models were made of each design and notch sizes varied to determine when and where fracture occurred. The results are shown in TABLE 1.

Referring to TABLE 1, the notch size 25%, 50% and 62.5% refer to the value of N60, N70, N80 relative to the width prior to forming the notch. The 0% notch means no notch was made in the crest. Thus, for example, the 50% notch size for Design A means T60 is one half the width prior to forming the notch. For each case, a radius notch is made, e.g., by using a laser after the pattern 10 is formed in the tube. The values 25%, 50%, and 62.5% therefore refer to a radius notch where after the notch is made the width T60, T70, T80 is equal to respectively 75%, 50% and 37.5% of the width prior to forming the notch. Prior to forming the notch, the crest 60, 70 and 80 width at the notch center location may be about, or may be 80% of the width of the crest, WC (FIG. 2A) which may be either the width of the trough 18$a$ or crest 16.

TABLE 1

| | fatigue acceleration, or drop in LFSF | | | |
|---|---|---|---|---|
| Notch size | 0% | 25% | 50% | 62.5% |
| Design A/straight crest (FIG. 3A) Fatigue Acceleration | 6% | 7% | 14% | 32% |
| Design B/inward angled crest (FIG. 3B) Fatigue Acceleration | 13% | 25% | 31% | 40% |
| Design C/outward angled crest (FIG. 3C) Fatigue Acceleration | 15%** | 14%** | 14%** | 15% |

Results are posted in terms of a percentage "fatigue acceleration" which means the expected amount of reduction in cycles of cyclic radial compressive loading needed in the ring 12 that will bring on fracture at the frangible crest (**—in these cases Design C did not show fracture first at the redundant crest). Alternatively, the % may be thought of as a drop in the fatigue safety factor for the stent ring, or decrease in the LFSF meaning one expects less cycles of radial loading to induce fracture. For example, assuming the stent adopts a fatigue safety factor of 3, Design A with 50% notch shows a drop in the safety factor at the point where fracture occurs (in this case at the point of minimum width T60) of 3*(1−0.14)=2.58. The 14% drop means one expects (statistically speaking) 14% fewer cycles to cause fracture of the notch. Note that even without a notch made the LFSF decrease for the Y-crown region is 6%, 13% or 15% depending on the crest design type, as intended, since the redundant crest is made at 80% of a strut, trough or crest width.

With regard to Design C, failure did not occur at the crest 80 when there was no notch, or a notch size of 25% or 50%. Rather, failure tended to occur in the strut portions 30$a''$ or 30$b''$ immediately to the right of the crest 80. Only when the notch size grew to 62.5% did failure occur at the crest 80. There also appears to be less capability to satisfy the other criteria, even if fracture occurred first at the crest 80. For these reasons, Design C would require further modification in order to satisfy all criteria (i)-(vi) for notch sizes less than 62.5%. For example, Design C width reduced to about, or to 50% or 40% of the crest or strut nominal width is expected to improve compliance with criteria (i)-(vi).

Designs A-B generally met the criteria (i)-(vi) with Design B being a more preferred choice. Design A may be more difficult to control than Design B. As can be appreciated from TABLE 1, there is very little, if any change in the drop in LFSF when there is no notch or a 25% notch for Design A. Additionally, the change in LFSF is more dramatic between a 50% and 62.5% change in notch size, then in the case of Design B. Design B, on the other hand, has a more gradual and monotonic drop in LFSF with increasing notch size, indicating that the inwardly angled crest 70 provides a more predictable change in LFSF than a straight or flat crest 60. Criteria (iv), while met by both Designs A and B, is better met by Design B than Design A in the presently preferred embodiment.

Additionally, a Y-crown adopting Design B is less prone to fractures occurring during the crimp. The stent can be crimped to a smaller diameter, or a larger diameter reduction, e.g., about 2.0 or 2.5 (the crest 50 presence in a Y-crown for Design A tends to more inhibit crimping because the struts 30a, 30b are not able to come together as much without causing fracture of the Y-crown). Design B can permit greater diameter reduction during crimp over Design A because of the structure of an inwardly directed crest, especially with no notch present, was found to reduce stress-concentrations in the stent ring during the crimp and when balloon-expanded since the angled surface tends to fold/unfold when the struts are brought together (crimp) or pushed apart (balloon expansion), respectively. Criteria (vi), while met by both Designs A and B, is better met by Design B than Design A in the presently preferred embodiment.

As indicated earlier, the redundant crest minimum width (prior to forming the notch) is 80% or about 80% of the width WC of a trough 18a, 18b or crest 16 (FIG. 2A). The value was selected based on the desire to have the crest fail before failure occurred in the adjacent strut structure, as well as cause a predictable decrease in LFSF with increasing notch size. Too thick a crest 50 (FIG. 2A) and the maximum stress would occur in the strut adjacent the redundant crest, since the strut would fail before either crests 16 or 50 failed. Essentially, in this case the effective strength of the combined crests 16 and 50 is higher than the struts 30.

Figure 2C:
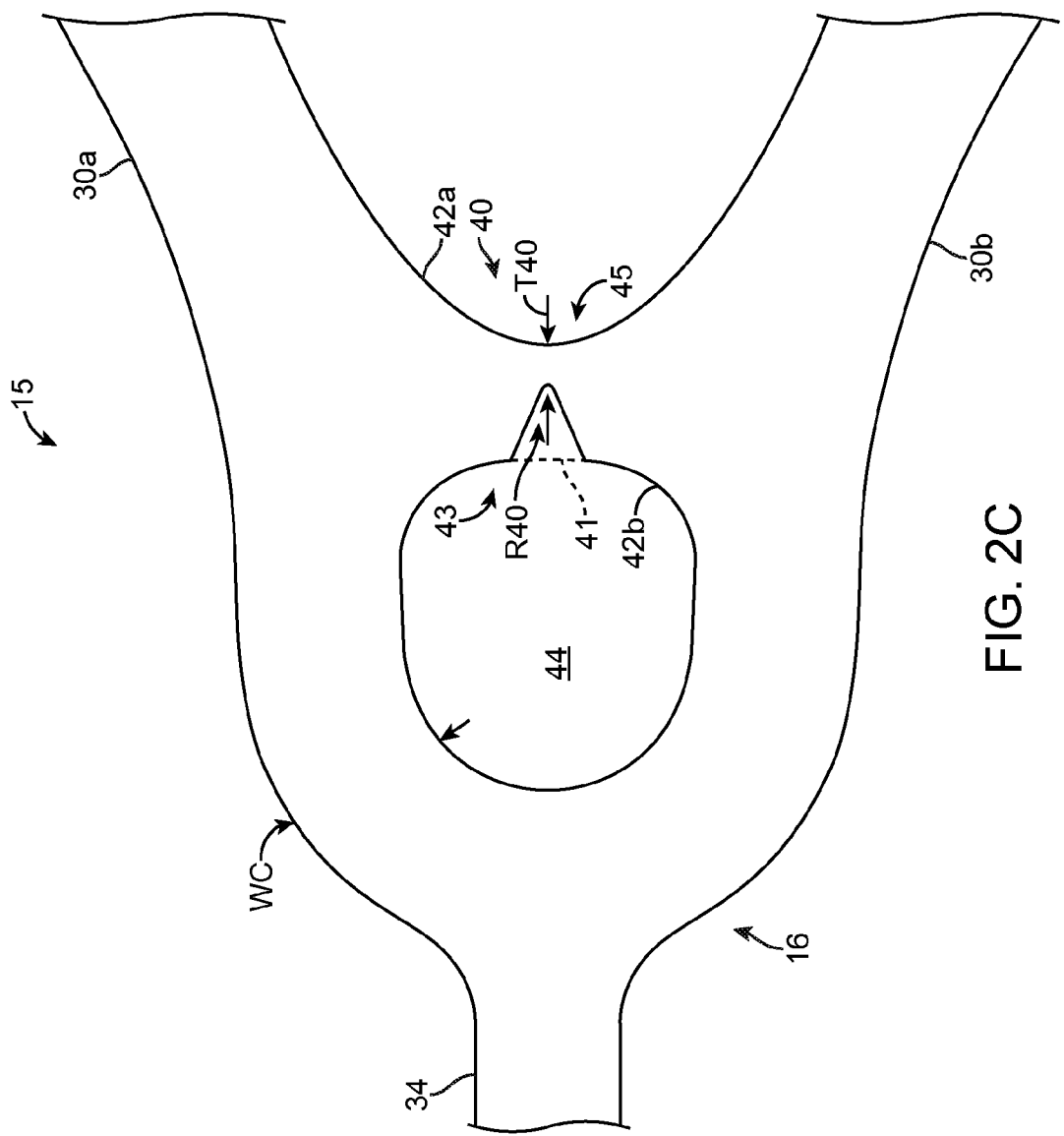
FIG. 2C shows the same Y-crown as FIGS. 2A-2B but with a radius notch replaced by a V notch for the redundant crest.

Referring to FIG. 2C, there is shown an alternative embodiment of a Y-crown showing a redundant crest 40 having a V-notch 43 rather than a radius notch. The V-notch 43 is made from the surface 41 of the member before forming the crest 40. The V-notch 43, in contrast to the radius notch 53, has a higher stress concentration due to its V-shape. As such, it is expected that the LFSF will decrease at least as much as the LFSF will decrease for the Design A, B and C for those cases where fracture occurs first at the crest. A V-notch is characterized by an inner radius R40 that is "about zero." For a stent cut from a tube with a laser, the term "about zero" means the minimum radius possible for the tool when cutting out the "V" shape. Being about zero, therefore, will mean that for a compressive load applied to the ring 12 the diverging walls of the V notch 43 will pull apart, which will first induce a fracture initiation at the place where the radius is about zero and more likely prior to the initiation of fracture for the radius notch 53. The reduction in LFSF for Design types A, B and C in TABLE 1 are expected to be at least the same, if not more accelerated for a V-notch, at least for those cases where fracture first occurred at the redundant crest.

Figure 6:
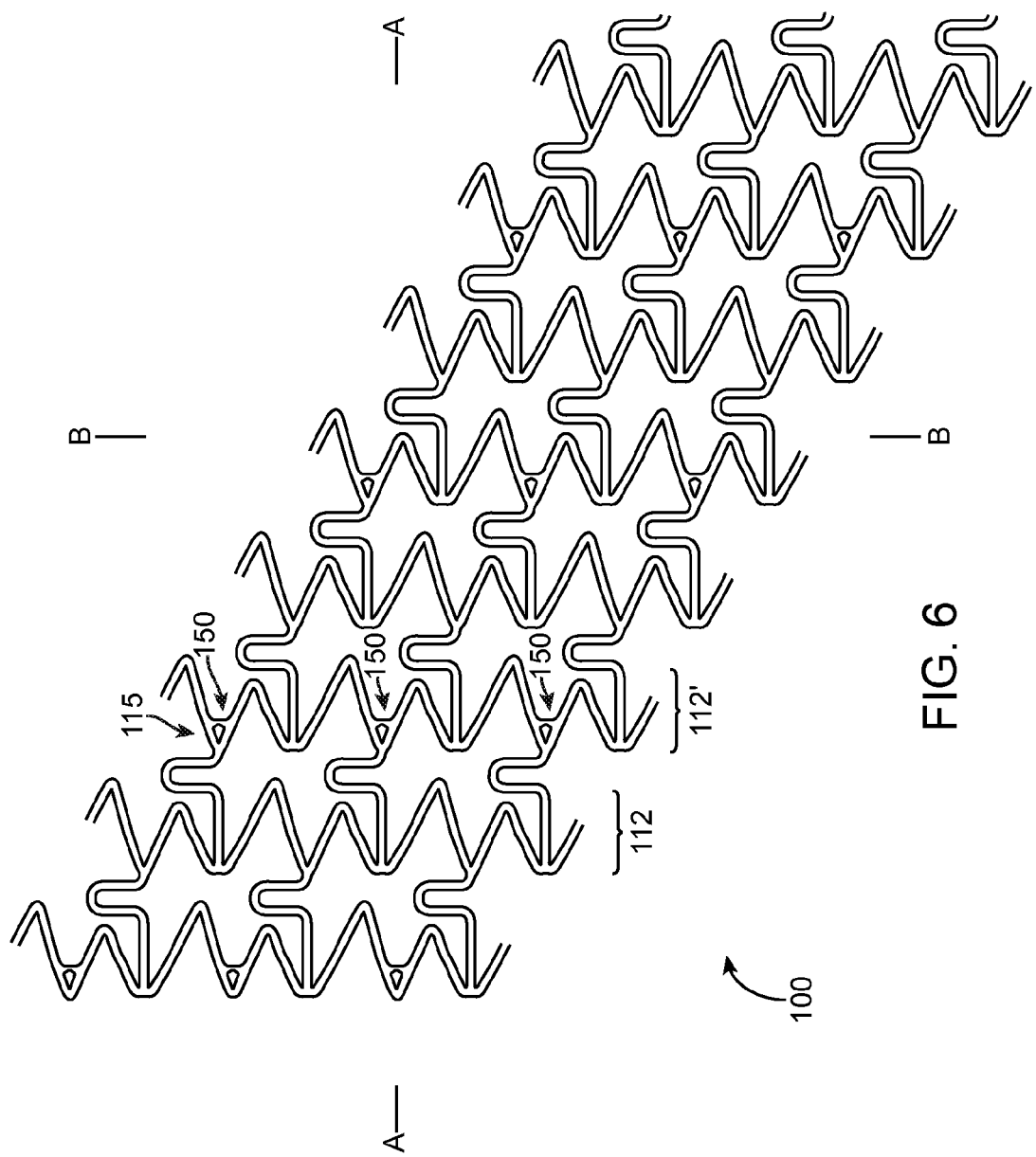
FIG. 6 shows an embodiment of a stent having some rings including redundant crests and some rings without redundant crests.

FIG. 6 shows an embodiment of a stent having one or more types of the redundant crests and or bridges as described above. Unless otherwise noted, the same element numbering means the same description applies. The figures are arranged in the same manner as FIG. 1, i.e., showing a repeating pattern of 6 crowns and 3 links between pairs of rings. Unless stated otherwise, it is understood that the embodiments of bridges and/or redundant crest types described above may apply to any of the stents patterns described below and shown in FIGS. 6-10.

FIG. 6 illustrates a stent 100 characterized by a ring 112' having redundant crests 150 at each Y-crown 115. Rings 112, 112' are connected to each other through links 190. According to these embodiments the stent 100 has a portion of rings devoid of redundant crests and another portion having redundant crests. A ring either has all Y-crowns 115 with a redundant crest 150 (ring 112') or no Y-crowns 115 with a redundant crest (ring 112). There may be 1, 2, 3 or 4 rings 12 without a crest 150 between each ring 112' with a crest 150. Having rings with and without a redundant crest (or different notch sizes from ring to the next) can serve the following purpose.

Fatigue fracture after so many cycles is generally speaking a rough approximation, since the occurrence of fracture depends on many variables. By having some rings with a redundant crest and some without, the rings designed to have fractures can be made with more fragile structure (i.e., thinner struts and/or higher notch sizes) thereby providing more guarantee that a fracture will occur, but without the risk of having a significant failure of the stent's overall radial strength prematurely. Thus, if a fragile ring (one with redundant crests) fails prematurely the ring without the fragile structure can provide the supporting role without the risk of total failure of the stent's radial support shortly after implantation. Additionally, for purposes of VRT it may only be necessary if only a local radial compliance is increased or radial stiffness removed by fracturing crests, rather than along the entire length of the stent. Alternating rings with and without redundant crests (e.g., ring without redundant crests between each ring with redundant crests) could bring about more gradual weakening of the total structure. Redundant crests in the middle of the stent could be used with longer outer bar arm lengths (like the compliance-matching ends) to allow for large cell opening with a side branch balloon without creating full discontinuities in the structure. (just redundant crest fractures).

It may be desired to have a more sparse (or fractured) structure in the middle of the stent to allow for easier access to a side branch through the stent. That is if the branching of a vessel originates from the middle portion of the stent. In some cases, it could branch near the proximal portion of the stent.

By breaking struts, a larger effective hole may be formed in the side structure of the stent, allowing for the subsequent passing of a device into a side branch. An issue here would be that the broken struts would be relatively unconstrained in the vicinity of a bifurcation, where flow dynamics are important.

A dynamically swinging strut could increase the risk of localized irritation (chronic strut motion and interaction with the vessel wall) and generate blood clots (thromboses). A structure that expands during side-cell opening with redundant crests and/or links that could crack open would increase the moment arm that hinges open more completely. This could occur to effectively widen the hole for side-cell opening (for side branch access), permitting a larger circular profile structure to pass through. A redundant structure, while doing this, would retain structural continuity, so remaining structural continuity would limit the motion of the broken strut faces.

Figure 7:
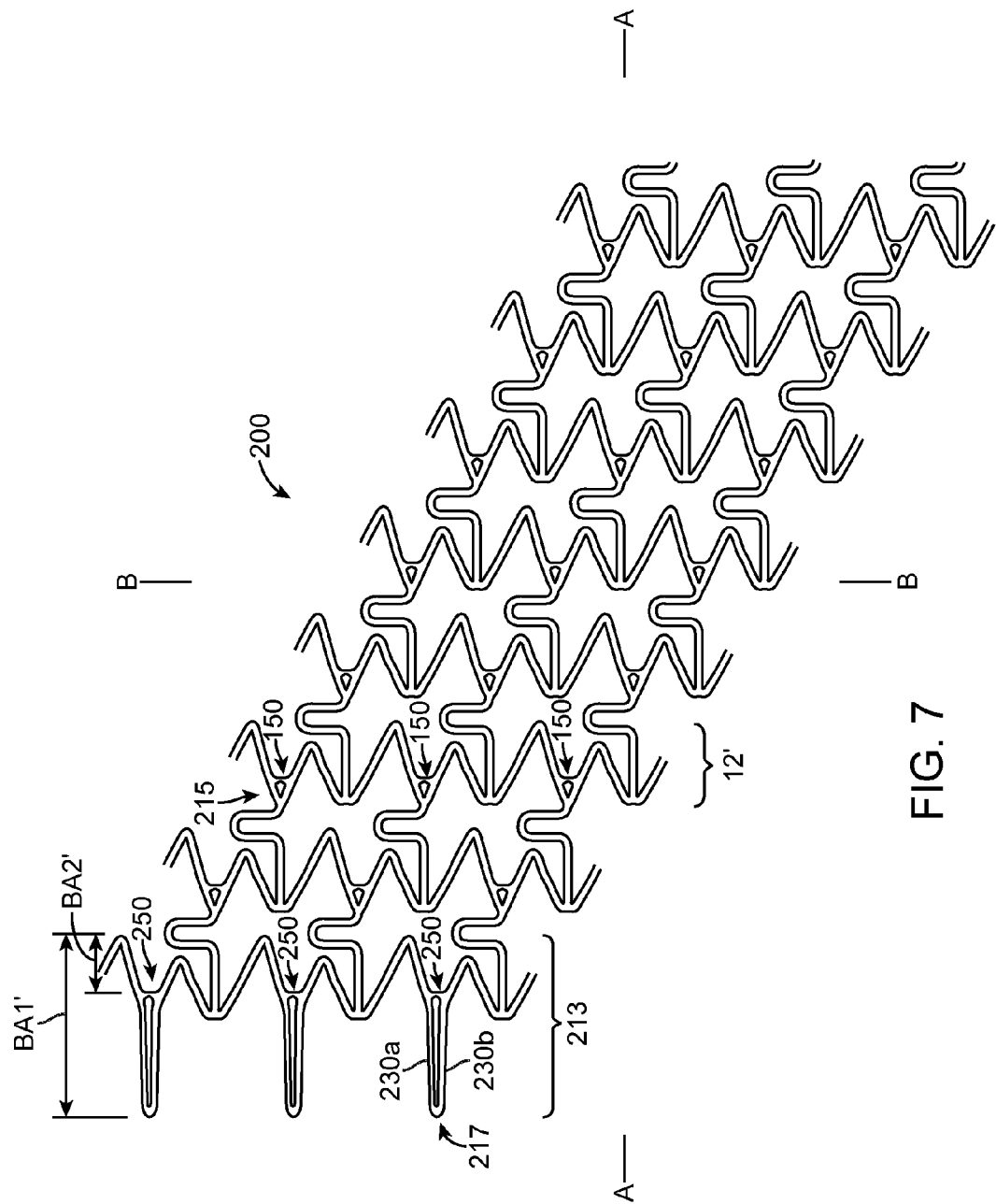
FIGS. 7-8 are two embodiments of an end-compliant stent having redundant crests at the end rings.
Figure 8:
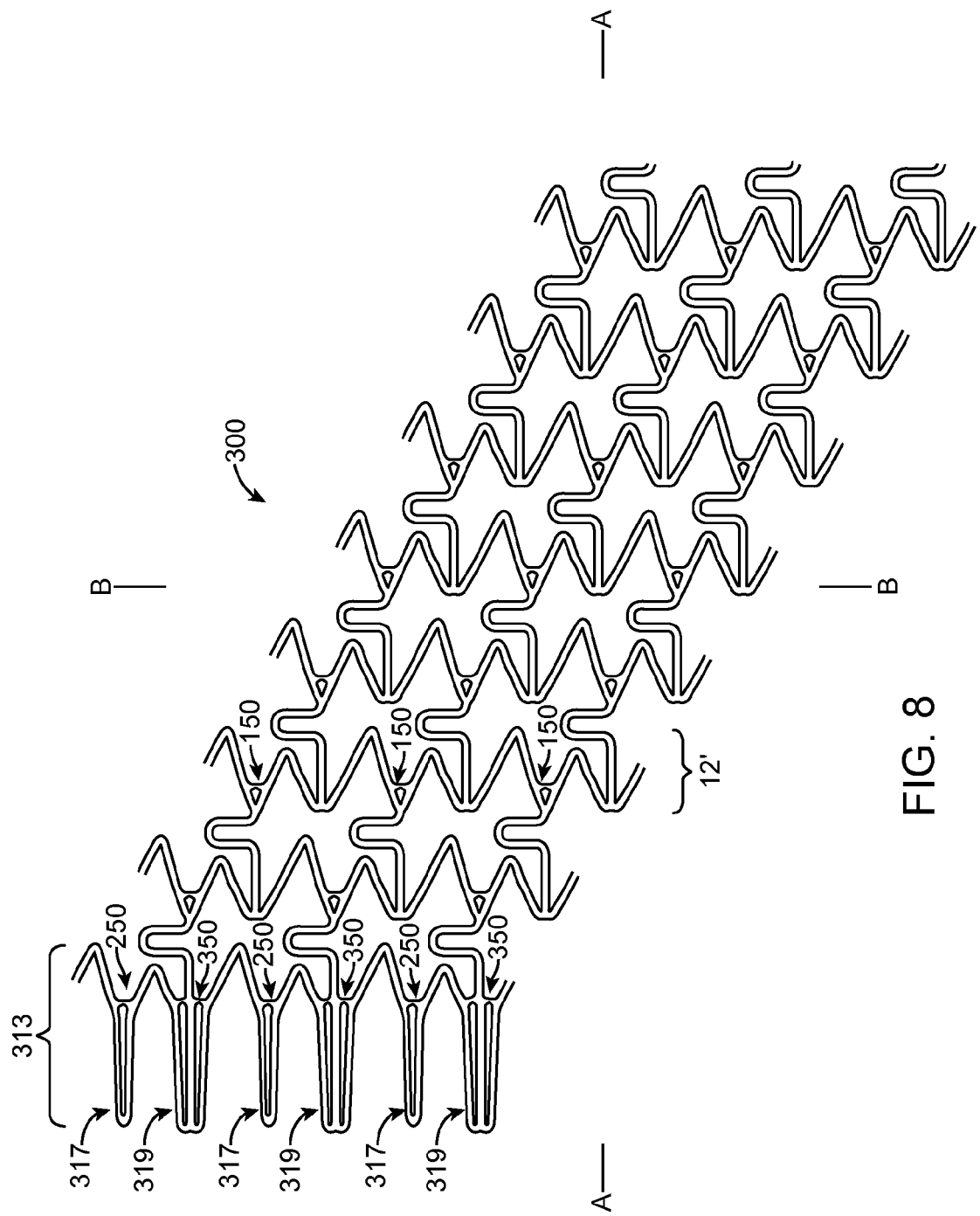

FIGS. 7 and 8 illustrate examples of stents 200, 300 where an end ring 212, 313 has a ring width BA1' substantially greater than the ring width BA1 of an interior or adjacent ring 12'. In these embodiments a redundant crest feature is provided at the end-rings of a stent or only at the end rings. Prior to fracture at the notch, the end rings may have a radial stiffness relatively equal to, about less than, about the same, or about greater than the radial stiffness of rings located inboard or in the middle of the stent structure. After fracture (or severing) at the notch the radial stiffness at the end rings is substantially less than the radial stiffness of interior or adjacent rings. As in prior embodiments, the redundant crest features include notch features to control the time frame of fracture of the redundant crest features. Therefore, a stent structure is disclosed that provides the desirable combination of high end-ring radial stiffness acutely and compliance matching behavior (and improved hemodynamics) months after deployment, as provided by the variable stiffness ring according to the disclosure.

FIGS. 7 and 8 illustrate examples of end-compliance matching stents 200, 300. There is shown wider end rings 213, 313 in these drawings. As such, the radial stiffness provided by rings 213, 313 at the end of the stent is significantly less than the radial stiffness for an end ring 12 for the stents of FIGS. 1 and 6 after redundant crests fail since the resulting bar arm length BA1' is higher than BA1 (after the notch fails, fractures or severs). Prior to notch failure the radial stiffness may be about the same as an interior ring 12 by making BA2 about equal to BA2'. In this case, the stent can possess the desired degree of high radial stiffness needed to maintain the vessel lumen during an acute period following implantation. For example, the stent at the end rings is capable of sustaining the needed minimal lumen diameter even during a period of plaque migration towards the stent ends.

FIG. 7 shows an end ring 213 with U-crowns 217 having a redundant crest 250 spanning between struts 230. The ratio BA2'/BA1' for the end ring after and before the crest 250 breaks may be significantly lower than BA2/BA1 with respect to the inner ring 12', for purposes of facilitating a desired radial stiffness matching; e.g., when the radial stiffness of the nearby unsupported native vessel is much less than the radial stiffness of the supported wall, then one may want BA2'/BA1' much less than BA2/BA1 so that there is a less abrupt change to radial stiffness properties near the end of the stent 200 or 300 while maintaining relatively high stiffness (at least within the first 6 months) for the middle portion of the stent. Moreover, one may want failure to occur much sooner for the end rings (e.g., choose notch size of greater than 50% as compared to less than 50% for an inner ring) when support is needed for a longer period but while imposing minimal length-wise impedence to vasomotion as the vessel heals. For example, BA2' is, or is about ½, ⅙, ⅓, ⅕, or ¼ of the length BA1' according to embodiments.

Accordingly, with respect to the peak radial stiffness of a Y-crown 15 of an interior ring, as discussed above, the ratio of bar arm lengths BA2'/BA1' for the end-ring 212, 313 may be substantially smaller than the ratio of bar arm lengths BA2/BA1 for the interior ring 12; BA2' is about equal to BA2 and BA1'>BA1; and/or there is a redundant crest only at the end rings. In the latter case the interior rings are devoid of a redundant crest. Or the redundant crest for an interior ring may have a smaller or larger notch size than the notch size of an end ring.

For both the stents 200 and 300 the redundant crest 250 located at the U-crown 217/317 may be the same as crest 50 (e.g., crests 60, 70 or 80) or crest 40 described earlier. For the stents described in FIGS. 7-8 the crest 150 may have a smaller or larger notch size than the crest 250 or 350 at the end ring. FIGS. 8A-8B describe aspects of an end-compliant stent 300 having a redundant crest at both a U-crown 317 and a W-crown 319. As between stents 200, 300 it may be desired to have the redundant crests at both the U-crowns and W-crowns to facilitate a greater change in radial stiffness following fracture of the redundant crests. This may be preferred so as to better avoid entanglements with devices passed through the lumen of the stent, or other issues arising during the acute period for an end-compliant stent, but while retaining the flexibility needed at the end ring after a period of patency, e.g., three-four months after the stent is implanted, for purposes of VRT.

A "peak-to-valley" link connection is shown in FIGS. 1, and 6-10. A "peak-to-peak" connection has links connecting so that only U-crowns and Y-crowns are present (no W-crowns). A "valley-to-valley" connection has links connecting so that only W-crowns and U-crowns are present (no Y-crowns). A "mid-strut" (off peak)-type connection has no links connecting adjacent rings at crests (or troughs). The disclosure is not limited to "peak-to-valley" link connections.

According to another aspect of the disclosure there are bridges formed in a U-shaped link element of a stent. The one or more bridges are designed as frangible elements that fracture prematurely, thereby providing a decrease over time in bending or axial stiffness, or variable stiffness following implantation. By providing one or more bridges in a link, the one or more links can be made to fail in a determined fashion, i.e., after a period of one week, one month, two months, etc.

Figure 5A:
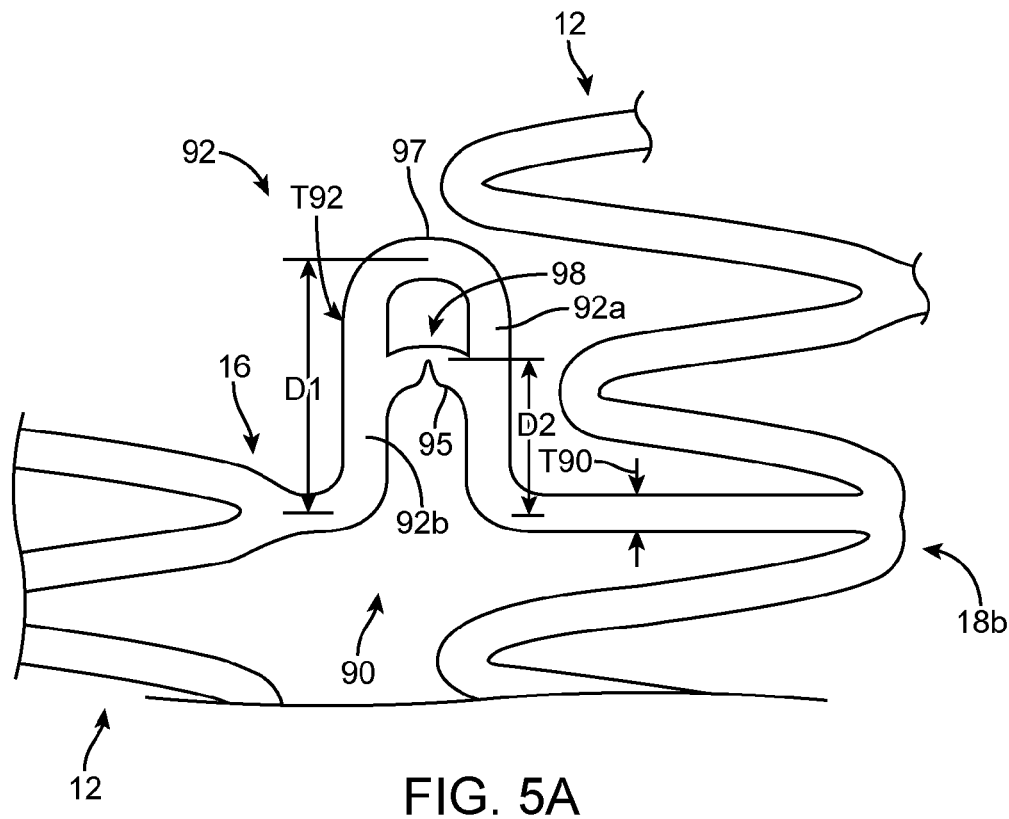

Referring to FIGS. 4A and 5A there are shown two embodiments of a stent having a single bridge 95 spanning between arms 92a, 92b of a U portion 92 of a link 90 connecting rings 12. The link 90 extends between adjacent rings 12 and connects a trough 18b of one ring 12 to a crest 16 of the other ring 12. Thus, there is a W-crown and Y-crown connection for the link 90 and the design is a "peak-to-valley" design for the stent. The U portion 92 is located closer the Y-crown than the W-crown. A change in bending stiffness of the link 90 when bridge 95 fractures may be, or is about (D2/D1). D1 is the circumferential (axis B-B in FIG. 1) distance from the bridge 95 neutral axis to the apex of the centerline of the crest 15 or trough 18b. D2 is the distance from the crest 97 apex neutral axis to the centerline of the crest 15 or trough 18b. The width T92 of U portion may be about, or is 80% of the width of the connecting or straight portion T90, or the crest 16. The ratio D2/D1 may be, or may be about ⅕, ¾, ⅘, ⅔, or ⅙.

The bridge 95 may also include a V-notch or radius notch 98. The notch 98 may be facing towards the crest 97 (FIG. 4A) so that axial compression or a negative bending moment applied by the right hand side ring 12 on the link 90 will tend to induce fracture (since the resultant deflection will tend to open the notch 98). Alternatively, the notch 98 may be facing away from the crest 97 (FIG. 5A) so that axial tension or a positive bending moment applied by the right hand side ring 12 on the link 90 will tend to induce fracture (since the resultant deflection will tend to open the notch 98).

Figure 4B:
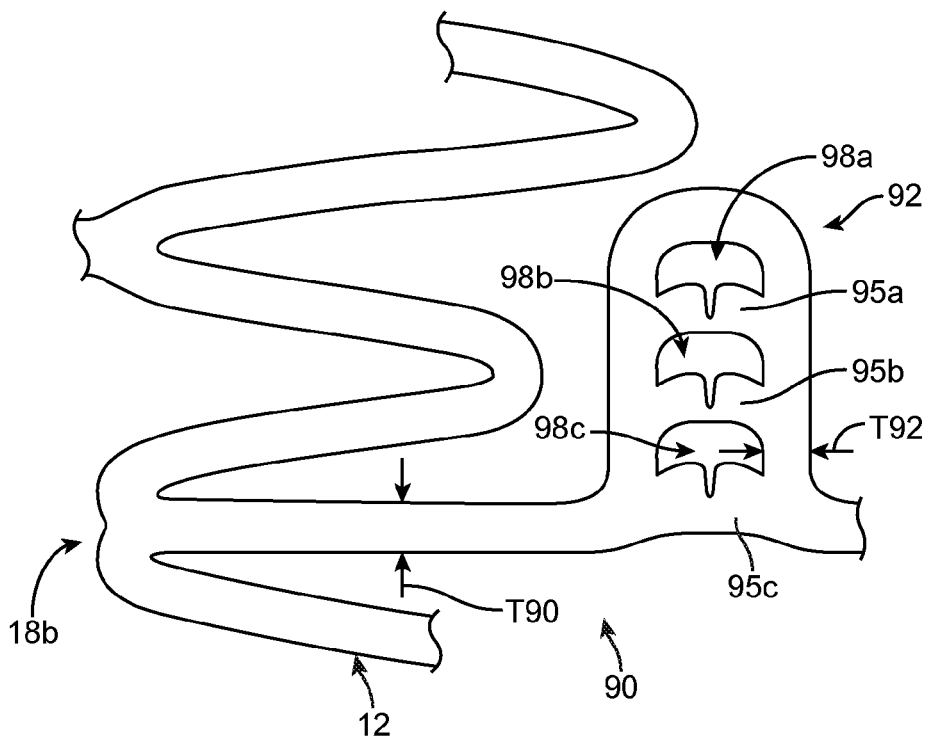
FIGS. 4B and 5B shows a link for a stent having three frangible bridges spanning a U portion. The notches face towards or away from the crest of the U portion.
Figure 5B:
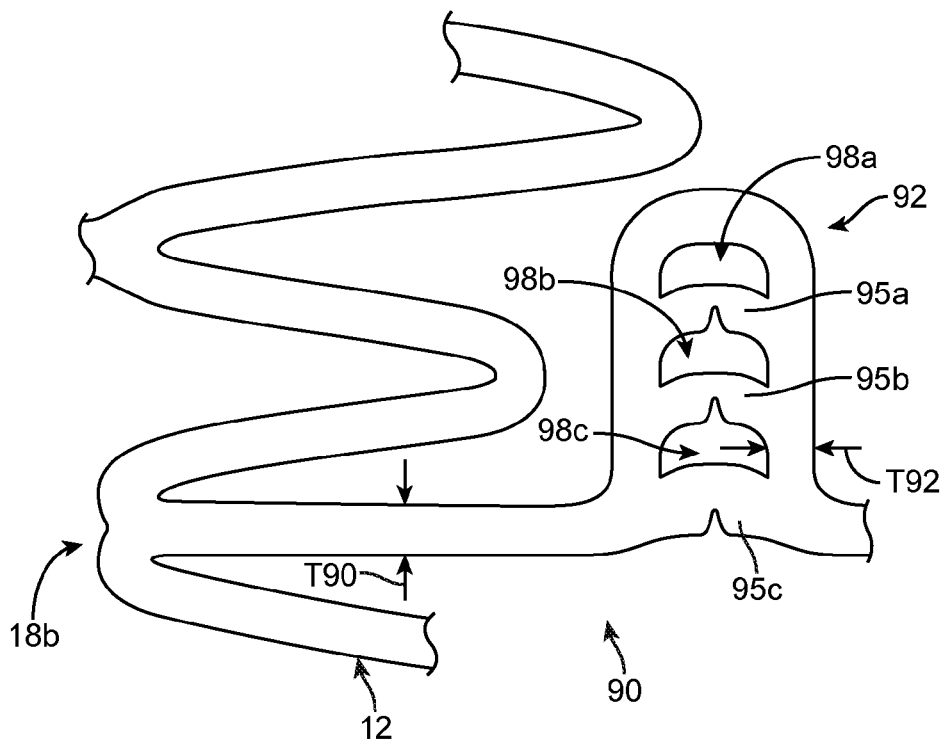

Referring to FIGS. 4B and 5B there are shown two embodiments of a stent having a three bridges 95 spanning between arms 92a, 92b of a U portion 92 of a link 90 connecting rings 12. As in the case of the single bridge embodiment, notches may face away or towards the crest 97. All other description is the same for each of the bridges 95a, 95b and 95c.

Additionally, for each of the notches 98a, 98b, 98c the sizes of the notch may vary. For example, the notch 98c may be deeper than the notch 98b so that the substantially higher axial stiffness provided by bridge 95c fractures quickly, e.g., within 1-2 weeks after implantation, whereas the bridge 95b fractures after a longer period, e.g., no sooner than 1 month. For example, the minimum width at notch 95c is ½ the minimum width at notch 95b and/or 95a.

Figure 9:
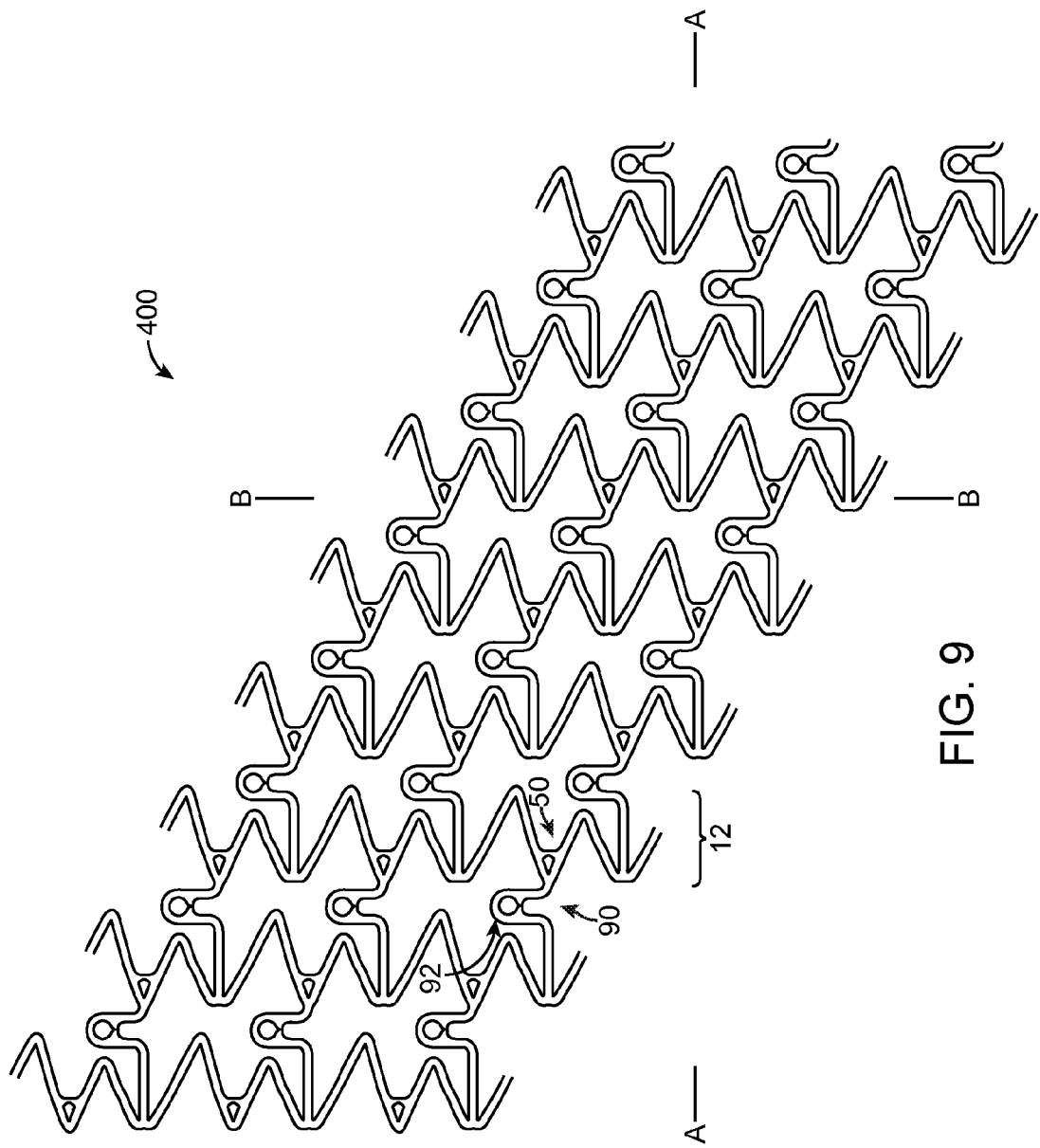
FIGS. 9-10 show two embodiments of a stent utilizing links having one or more frangible bridges as shown in FIGS. 4A, 4B, 5A and 5B.
Figure 10:
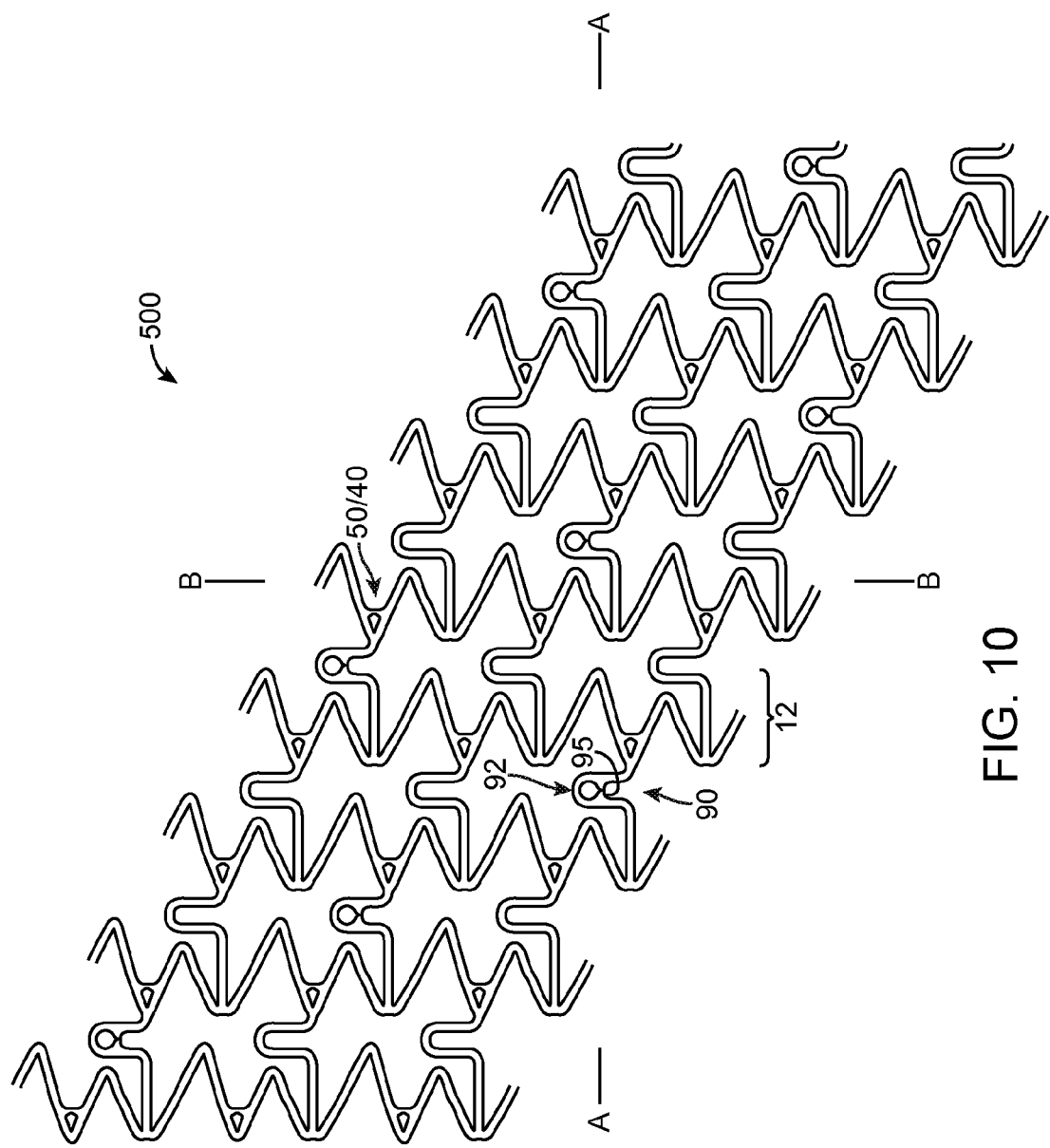

FIGS. 9-10 show two embodiments of a stent patterns utilizing links having one or more bridges. FIG. 9 shows a stent 400 with every Y-crown having a redundant crest 50 or 40 and every link 90 having a U portion 97 with bridge 95. The link 90 may take the form of any of the embodiments described above in connection with FIGS. 4-5. FIG. 10 shows a stent 500 that is the same as stent 400, except that only one of the three links 90 connecting rings includes one or more frangible bridges. The link 90 with bridge 95 may take the form of any of the embodiments described above in connection with FIGS. 4-5.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent having a circumference and an axis, comprising:
    a pattern of interconnected elements forming a plurality of rings made of a non-biodegrading material wherein rings comprise struts, rings are connected to adjacent rings by links and each ring extends about the circumference in an undulating pattern of alternating peaks and valleys; and
    at least one of the peaks and valleys comprising:
        an outer crest of a peak and an outer trough of a valley, wherein a distance between the outer crest and the outer trough is a width of the ring,
        a first strut extending from the outer crest to the outer trough of a first adjacent valley and a second strut extending from the outer crest to the outer trough of a second adjacent valley,
        a redundant crest integral to the peak, located between the outer crest and the outer trough of the first adjacent valley and extending between the first and second struts,
        the redundant crest including a notch,
        a first radial stiffness when the notch is severed, and
        a second radial stiffness, higher than the first radial stiffness, when the notch has not severed,
        wherein the peak is configured such that the outer crest is capable of carrying radial loads between the first and second struts after the redundant crest substantially fails.

2. The stent of claim 1, wherein the stent includes end-rings and an interior ring located between the end rings, wherein the interior ring is devoid of a redundant crest and has a first bar arm length, and after a notch of at least one of the end rings sever, a bar arm length of the end ring increases from a second bar arm length to a third bar arm length,
    wherein the third bar arm length is substantially greater than the first and second bar arm lengths.

3. The stent of claim 1, wherein the stent includes end-rings and an interior ring located between the end rings, wherein the width of an end ring is greater than the width of the interior ring, wherein both an end ring peak and an interior ring peak have a redundant crest including a notch; and wherein
    the end ring peak has first and second bar arm lengths before and after, respectively, the notch severs, and
    the interior ring peak includes third and fourth bar arm lengths before and after, respectively, the notch severs,
    wherein the first and third bar arm lengths are about equal and the second bar arm length is greater than the fourth bar arm length.

4. The stent of claim 3, wherein the end ring notch is larger than the interior ring notch.

5. The stent of claim 1, wherein the notch has an inner radius of about zero, or the redundant crest, outer crest and struts form a closed space.

6. The stent of claim 1, wherein the redundant crest forms a substantially straight surface or continuous curve portion along an edge of the closed space, or the redundant crest is angled inwards towards the outer crest.

7. The stent of claim 1, wherein a link connects a peak to a valley.

8. The stent of claim 1, wherein the links are U-shaped links comprising a U-portion disposed between a first and second ring, and wherein a U-shaped link comprises:
    one or more frangible bridges spanning between arms of the U-portion, and straight portions connecting the U-portion to each of the first and second rings.

9. The stent of claim 8, wherein the one or more bridges have a width of about 80% of the width of a straight portion or the U-portion of the U-shaped link.

10. The stent of claim 9, wherein the one or more bridges include a notch facing towards and/or away from the U-portion.

11. The stent of claim 1, wherein the notch reduces the thickness of the redundant crest by about 25%, 50% or 62.5%.

12. The stent of claim 1, the redundant crest comprising a structure configured for fracturing at the notch prior to fracture at a strut portion adjacent the redundant crest, the structure including:
    a redundant crest width that is about 80% of the width of the first strut, the width of the outer crest or width of the outer trough, and
    a redundant crest notch width that is about 25%, 50% or 62.5% of the redundant crest width.

13. The stent of claim 1, the redundant crest comprising a structure configured for fracturing at the notch prior to fracture at a strut portion adjacent the redundant crest, the structure including a notch width that is about, or is at most 60% of a width of the first strut, the outer crest or outer trough.

14. A method for crimping the stent of claim 1 to a balloon of a balloon catheter, including the steps of reducing the diameter of the stent by plastic deformation of the stent,
    wherein the stent has a pre-crimp diameter before crimping and a fully crimped diameter after crimping, and
    wherein the ratio of pre-crimp to fully crimped diameters is at least about 2.

15. The method of claim 14, wherein the redundant crest is angled towards the outer crest.

16. The stent of claim 1, the redundant crest comprising a structure configured for fracturing at the notch prior to fracture at a strut portion adjacent the redundant crest,
wherein the peak defines a closed space formed by a portion of the first and second struts, the redundant crest and the outer crest, wherein the redundant crest is straight, angled away from the outer crest or angled towards the outer crest.

17. The stent of claim 16, wherein the redundant crest is angled towards the outer crest, the notch size is about 25%, 50% or 62.5% of the redundant crest width and the lowest fatigue safety factor (LFSF) decreases monotonically with increasing notch size.

18. The stent of claim 17, wherein the redundant crest width is about 80% of an outer crest width or a first strut width.

19. A stent, comprising:
a pattern of interconnected elements forming a plurality of rings made of a nonbiodegrading material wherein rings comprise struts, rings are connected to adjacent rings by links and each ring extends about the circumference in an undulating pattern of alternating peaks and valleys;
at least one of the rings comprising a variable stiffness ring wherein the variable stiffness ring comprises:
an outer crest and an outer trough of a valley, wherein a distance between the outer crest and the outer trough is a width of the ring,
a first strut extending from the outer crest to the outer trough of a first adjacent valley and a second strut extending from the outer crest to the outer trough of a second adjacent valley,
a redundant crest integral to the peak, located between the outer crest and the outer trough of the first adjacent valley and, the redundant crest extending between the first and second struts, and
the redundant crest including a notch,
wherein surfaces of the redundant crest, outer crest and opposed portions of the first and second struts circumscribe a closed space;
wherein a radial stiffness of the peak is proportional to a bar arm length between a load-bearing valley crest and a load-bearing peak crest, so that the variable stiffness ring has a first stiffness when the redundant crest is severed at the notch, and a second stiffness when the redundant crest has not severed at the notch, the second stiffness being higher than the first stiffness, and
wherein the peak is configured such that the outer crest is capable of carrying radial loads between the first and second struts after the redundant crest substantially fails.

20. The stent of claim 19,
wherein the rings comprise a pair of end rings and rings adjacent and interior to the end rings, the end rings comprising a variable stiffness ring at only the end rings; or
wherein the stent includes a pair of end rings and rings adjacent and interior to the end rings, the end rings comprising a first variable stiffness and the inner rings comprising a second variable stiffness, different from the first variable stiffness, such that the radial stiffness of the end rings is substantially lower than the radial stiffness of the inner rings after the redundant crests substantially fail for the end and inner rings.

21. The stent of claim 20, wherein the end rings have a first variable stiffness and the interior rings have a second and a third variable stiffness, different from each other and each being substantially greater than the first variable stiffness after the respective redundant crests substantially fail.

* * * * *